(12) United States Patent
Vela Hernandez et al.

(10) Patent No.: US 9,789,117 B2
(45) Date of Patent: Oct. 17, 2017

(54) USE OF SIGMA LIGANDS IN DIABETES TYPE-2 ASSOCIATED PAIN

(75) Inventors: Jose Miguel Vela Hernandez, Barcelona (ES); Maria Isabel Martin Fontelles, Madrid (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 0 days.

(21) Appl. No.: 14/118,704

(22) PCT Filed: May 18, 2012

(86) PCT No.: PCT/EP2012/059232
§ 371 (c)(1),
(2), (4) Date: Nov. 19, 2013

(87) PCT Pub. No.: WO2012/156497
PCT Pub. Date: Nov. 22, 2012

(65) Prior Publication Data
US 2014/0107111 A1    Apr. 17, 2014

(30) Foreign Application Priority Data
May 18, 2011   (EP) .................................. 11382157

(51) Int. Cl.
| | | |
|---|---|---|
| A61K 31/54 | (2006.01) | |
| A61K 31/541 | (2006.01) | |
| A61K 31/4523 | (2006.01) | |
| A61K 31/4725 | (2006.01) | |
| A61K 31/496 | (2006.01) | |
| A61K 31/5377 | (2006.01) | |
| A61K 45/06 | (2006.01) | |
| A61K 31/415 | (2006.01) | |
| A61K 31/4155 | (2006.01) | |
| A61K 31/4178 | (2006.01) | |
| A61K 31/454 | (2006.01) | |
| A61K 31/4545 | (2006.01) | |
| C07D 231/22 | (2006.01) | |
| C07D 401/12 | (2006.01) | |
| C07D 403/12 | (2006.01) | |
| C07D 471/04 | (2006.01) | |

(52) U.S. Cl.
CPC .......... *A61K 31/541* (2013.01); *A61K 31/415* (2013.01); *A61K 31/4155* (2013.01); *A61K 31/4178* (2013.01); *A61K 31/454* (2013.01); *A61K 31/4523* (2013.01); *A61K 31/4545* (2013.01); *A61K 31/4725* (2013.01); *A61K 31/496* (2013.01); *A61K 31/5377* (2013.01); *A61K 45/06* (2013.01); *C07D 231/22* (2013.01); *C07D 401/12* (2013.01); *C07D 403/12* (2013.01); *C07D 471/04* (2013.01)

(58) Field of Classification Search
USPC ........................ 514/227.8, 236.5, 407, 326
See application file for complete search history.

(56) References Cited

U.S. PATENT DOCUMENTS

| | | | |
|---|---|---|---|
| 2,908,677 | A | 10/1959 | Straley |
| 3,514,439 | A | 5/1970 | Wehrli et al. |
| 3,980,675 | A | 9/1976 | Venturella et al. |
| 4,024,175 | A | 5/1977 | Satzinger et al. |
| 4,207,392 | A | 6/1980 | Shiao et al. |
| 4,234,479 | A | 11/1980 | Mennicke et al. |
| 4,234,616 | A | 11/1980 | Shu et al. |
| 4,337,263 | A | 6/1982 | Techer et al. |
| 5,948,777 | A | 9/1999 | Bender et al. |
| 6,057,371 | A | 5/2000 | Glennon |
| 6,100,259 | A | 8/2000 | Xiang et al. |
| 6,166,072 | A | 12/2000 | Bell et al. |
| 6,492,529 | B1 | 12/2002 | Kapadia et al. |
| 6,509,367 | B1 | 1/2003 | Choon-Moon |
| 7,091,257 | B2 | 8/2006 | Greer, IV |
| 7,105,646 | B2 | 9/2006 | Chamberlain et al. |

(Continued)

FOREIGN PATENT DOCUMENTS

| | | |
|---|---|---|
| EP | 0248594 A2 | 12/1987 |
| EP | 0414289 A1 | 2/1991 |

(Continued)

OTHER PUBLICATIONS

Laboratoire Roger bellon's CAS: 87: 5959, 1977.*
International Search Report issued Jun. 26, 2012 in PCT/EP2012/059232.
C. A. Abbott, et al., "The North-West Diabetes Foot Care Study: incidence of, and risk factors for, new diabetic foot ulceration in a community-based patient cohort", Diabetic Medicine, vol. 19, 2002, pp. 377-384.
Andrew J. M. Boulton, et al., "Diabetic Neuropathies" Diabetes Care, vol. 28, No. 4, Apr. 2005, pp. 956-962.

(Continued)

*Primary Examiner* — Rei-Tsang Shiao
(74) *Attorney, Agent, or Firm* — Oblon, McClelland, Maier & Neustadt, L.L.P.

(57) ABSTRACT

The invention refers to the use of a sigma ligand, particularly a sigma ligand of formula (I) to prevent and/or treat type-2 diabetes-associated pain and related symptoms.

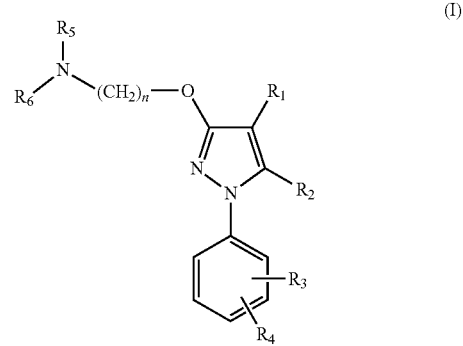

6 Claims, 5 Drawing Sheets

(56) References Cited

U.S. PATENT DOCUMENTS

| | | |
|---|---|---|
| 7,696,199 B2 | 4/2010 | Laggner et al. |
| 7,799,782 B2 * | 9/2010 | Munson et al. ........... 514/234.5 |
| 7,988,966 B2 | 8/2011 | Pavone |
| 8,193,223 B2 | 6/2012 | Jagerovic et al. |
| 8,293,740 B2 * | 10/2012 | Laggner ............... A61K 31/415 514/235.8 |
| 8,314,096 B2 * | 11/2012 | Laggner ............... A61K 31/415 514/231.5 |
| 8,470,867 B2 | 6/2013 | Laggner et al. |
| 8,492,425 B2 | 7/2013 | Torrens Jover et al. |
| 8,877,753 B2 | 11/2014 | Buschmann |
| 2001/0036951 A1 | 11/2001 | Farrar et al. |
| 2003/0144309 A1 | 7/2003 | Choon-Moon |
| 2005/0020483 A1 | 1/2005 | Oksenberg |
| 2006/0106068 A1 | 5/2006 | Laggner |
| 2007/0208134 A1 | 9/2007 | Hunter et al. |
| 2008/0058362 A1 | 3/2008 | Singh et al. |
| 2008/0125416 A1 | 5/2008 | Laggner et al. |
| 2008/0161604 A1 | 7/2008 | Calvani et al. |
| 2009/0018151 A1 | 1/2009 | Fink |
| 2009/0264442 A1 | 10/2009 | Cuberes-Aitisent et al. |
| 2009/0325975 A1 | 12/2009 | Buschmann |
| 2010/0081659 A1 | 4/2010 | Laggner |
| 2010/0190078 A1 * | 7/2010 | Rapaport et al. ............. 429/444 |
| 2010/0190780 A1 | 7/2010 | Laggner et al. |
| 2010/0190781 A1 * | 7/2010 | Laggner ............... A61K 31/415 514/227.8 |
| 2010/0240711 A1 | 9/2010 | Takada et al. |
| 2011/0112095 A1 | 5/2011 | Buschmann et al. |
| 2011/0269727 A1 | 11/2011 | Toledano |
| 2012/0141606 A1 | 6/2012 | Baeyens-Cabrera et al. |
| 2012/0232093 A1 | 9/2012 | Cuberes-Altisent et al. |
| 2012/0283262 A1 | 11/2012 | Soler Ranzani et al. |
| 2012/0302568 A1 | 11/2012 | Vela Hernandez et al. |
| 2012/0316336 A1 | 12/2012 | Berenguer Maimo et al. |
| 2013/0109692 A1 | 5/2013 | Vela Hernandez et al. |
| 2013/0143884 A1 | 6/2013 | Cuberes-Aitisent et al. |
| 2013/0158033 A1 | 6/2013 | Hernandez |
| 2013/0324535 A1 | 12/2013 | Zamanillo-Castanedo et al. |
| 2015/0018354 A1 | 1/2015 | Buschmann et al. |
| 2016/0220575 A1 | 8/2016 | Baeyens-Cabrera et al. |

FOREIGN PATENT DOCUMENTS

| | | |
|---|---|---|
| EP | 0431943 A2 | 6/1991 |
| EP | 0445974 A2 | 9/1991 |
| EP | 0518805 A1 | 12/1992 |
| EP | 0529973 A1 | 3/1993 |
| EP | 0441333 B1 | 5/1994 |
| EP | 0975648 A1 | 2/2000 |
| EP | 1130018 A1 | 9/2001 |
| EP | 1634872 A1 | 3/2006 |
| EP | 1634873 A1 | 3/2006 |
| EP | 1 787 679 A1 | 5/2007 |
| EP | 1829866 A1 | 9/2007 |
| EP | 1829875 A1 | 9/2007 |
| EP | 1847542 A1 | 10/2007 |
| EP | 2090311 A1 | 8/2009 |
| EP | 2112139 A1 | 10/2009 |
| EP | 2113501 A1 | 11/2009 |
| EP | 2116539 A1 | 11/2009 |
| EP | 2353598 A1 | 8/2010 |
| EP | 2254579 A1 | 12/2010 |
| EP | 2 292 236 A1 | 3/2011 |
| EP | 2353591 A1 | 8/2011 |
| EP | 2361904 A1 | 8/2011 |
| EP | 2415471 A1 | 2/2012 |
| EP | 2335688 A1 | 6/2012 |
| EP | 2460519 A1 | 6/2012 |
| EP | 2460804 A1 | 6/2012 |
| EP | 2524694 A1 | 11/2012 |
| EP | 2395003 A1 | 12/2012 |
| EP | 2426111 A1 | 3/2013 |
| EP | 2426112 A1 | 3/2013 |
| EP | 2792352 A1 | 10/2014 |
| EP | 2818166 A1 | 12/2014 |
| EP | 3043795 A1 | 7/2016 |
| EP | 3082790 A1 | 10/2016 |
| ES | 2251316 A1 | 10/2004 |
| FR | 2301250 A1 | 9/1976 |
| FR | 2472564 A1 | 7/1981 |
| GB | 1088973 A | 10/1967 |
| GB | 1496411 A1 | 12/1977 |
| GB | 2026482 A1 | 7/1987 |
| IL | 151533 B | 3/2008 |
| JP | 1992/364129 | 12/1992 |
| JP | 10036259 | 2/1998 |
| JP | 10055048 | 2/1998 |
| JP | 2004/196678 | 7/2004 |
| JP | 2008/510767 | 4/2008 |
| JP | 2008-179541 | 8/2008 |
| RU | 2218187 C2 | 10/2003 |
| RU | 2322977 C1 | 4/2008 |
| RU | 2382646 C1 | 2/2010 |
| SU | 11248 A1 | 9/1929 |
| WO | WO-91/09594 A1 | 7/1991 |
| WO | WO-92/09560 A1 | 6/1992 |
| WO | WO-93/23383 A1 | 12/1992 |
| WO | WO-1996/016063 A1 | 5/1996 |
| WO | WO-1998/046618 A1 | 10/1998 |
| WO | WO-99/01444 A1 | 1/1999 |
| WO | WO-99/21824 A1 | 5/1999 |
| WO | WO-99/31057 A1 | 6/1999 |
| WO | WO-99/31074 A2 | 6/1999 |
| WO | WO-99/31075 A1 | 6/1999 |
| WO | WO-1999/059409 A1 | 11/1999 |
| WO | WO-99/61424 A1 | 12/1999 |
| WO | WO-00/31020 A1 | 2/2000 |
| WO | WO-00/20005 A1 | 4/2000 |
| WO | WO 00/27394 A1 | 5/2000 |
| WO | WO-00/40275 A2 | 7/2000 |
| WO | WO-00/73259 A1 | 12/2000 |
| WO | WO-00/73296 A2 | 12/2000 |
| WO | WO-00/73300 A1 | 12/2000 |
| WO | WO-02/085839 A1 | 10/2002 |
| WO | WO-02/092573 A2 | 11/2002 |
| WO | WO-02/102387 A1 | 12/2002 |
| WO | WO-2003/080183 A1 | 10/2003 |
| WO | WO-2004/016592 A1 | 2/2004 |
| WO | WO-2004/017961 A1 | 3/2004 |
| WO | WO-2004/046129 A2 | 6/2004 |
| WO | WO-2005/061462 A2 | 7/2005 |
| WO | WO-2006/010587 A1 | 2/2006 |
| WO | WO-2006/021462 A1 | 3/2006 |
| WO | WO-2006/021463 A1 | 3/2006 |
| WO | WO-2006/027221 A1 | 3/2006 |
| WO | WO-2006/118307 A1 | 11/2006 |
| WO | WO-07/002559 A1 | 1/2007 |
| WO | WO-2007/025613 A2 | 3/2007 |
| WO | WO-2007/046550 A1 | 4/2007 |
| WO | WO-07/079086 A1 | 7/2007 |
| WO | WO-2007/090661 A2 | 8/2007 |
| WO | WO-07/098964 A2 | 9/2007 |
| WO | WO-07/108517 A1 | 9/2007 |
| WO | WO-2007/098939 A1 | 9/2007 |
| WO | WO-2007/098953 A1 | 9/2007 |
| WO | WO-2007/098963 A1 | 9/2007 |
| WO | WO-2007/110221 A1 | 10/2007 |
| WO | WO 2007/141018 A1 | 12/2007 |
| WO | WO-2008/015266 A1 | 2/2008 |
| WO | WO-2008/055932 A1 | 5/2008 |
| WO | WO-2008/108517 A1 | 9/2008 |
| WO | WO-2008/149062 A1 | 12/2008 |
| WO | WO-2009/038112 A1 | 3/2009 |
| WO | WO-2009/071657 A1 | 6/2009 |
| WO | WO-2009/103487 A1 | 8/2009 |
| WO | 2009/130331 | 10/2009 |
| WO | WO 2009/130310 A1 | 10/2009 |
| WO | WO-2009/130314 A1 | 10/2009 |
| WO | WO-2011/095579 A1 | 1/2011 |
| WO | 2011/018487 | 2/2011 |
| WO | WO-2011064315 A1 | 6/2011 |
| WO | WO-2011/095585 A1 | 8/2011 |

(56) References Cited

FOREIGN PATENT DOCUMENTS

| WO | WO-2011095584 A1 | 8/2011 |
|---|---|---|
| WO | WO-2011/144721 A1 | 11/2011 |
| WO | WO-2011/147910 A1 | 12/2011 |
| WO | WO-2012/016980 A1 | 2/2012 |
| WO | WO-2012/019984 A1 | 2/2012 |
| WO | WO-2012/072781 A1 | 6/2012 |
| WO | WO-2012/072782 A1 | 6/2012 |
| WO | WO-2012/156497 A1 | 11/2012 |
| WO | WO-2012/158413 A1 | 11/2012 |
| WO | WO-2014/170319 A1 | 10/2014 |
| WO | WO-2014/207024 A1 | 12/2014 |
| WO | WO-2015/036470 A1 | 3/2015 |
| WO | WO-2015/091505 A1 | 6/2015 |
| WO | WO-2015/091508 A1 | 6/2015 |

OTHER PUBLICATIONS

Susan B. Hellewell, et al., "A sigma-like binding site in rat pheochromocytoma (PC12) cells: decreased affinity for (+)—benzomorphans and lower molecular weight suggest a different sigma receptor form from that of guinea pig brain", Brain research, vol. 527, 1990, pp. 244-253.

Giuseppe Ronsisvalle, et al., "Opioid and sigma receptor studies. New developments in the design of selective sigma ligands" Pure Appl. Chem., vol. 73, No. 9, 2001, pp. 1499-1509.

Desu Chen, et al., "Development and application of rodent models for type 2 diabetes", Diabetes, Obesity and Metabolism, vol. 7, 2005, pp. 307-317.

C. Daousi, et al., "Chronic painful peripheral neuropathy in an urban community: a controlled comparison of people with and without diabetes", Diabetic Medicine, vol. 21, 2004, pp. 976-982.

Fei Li, et al., "Taurine reverses neurological and neurovascular deficits in Zucker diabetic fatty rats", Neurobiology of Disease, vol. 22, 2006, pp. 669-676.

Jacob E. Friedman, et al., Altered expression of muscle glucose transporter GLUT-4 in diabetic fatty Zucker rats (ZDF/Drt-fa), American Physiological Society, 1991, E782-E788.

Adam Gordois, et al., "The Health Care Costs of Diabetic Peripheral Neuropathy in the U.S.", Diabetes Care, vol. 26, No. 6, Jun. 2003, pp. 1790-1795.

Melanie L. Leitner, et al., "Regional variation in the ratio of $\sigma_1$ to $\sigma_2$ binding in rat brain", European Journal of Pharmacology, vol. 259, 1994, pp. 65-69.

Puttur D. Prasad, et al., "Exon-Intron Structure, Analysis of Promoter Region, and Chromosomal Localization of the Human Type 1 σ Receptor Gene", Journal of Neurochemistry, vol. 70, 1998, pp. 443-451.

Merskey et al., "Part III: Pain Terms, A Current List with Definitions and Notes on Usage", Classification of Chronic Pain, 1994, pp. 210-213.

Christine L. Oltman, et al., "Progression of vascular and neural dysfunction in sciatic nerves of Zucker diabetic fatty and Zucker rats", Am. J. Physiol. Endocrinol. Metab., vol. 289, 2005, pp. E113-E122.

Ann Noelle Poncelet, "Risk factors, patterns of presentation, diagnosis, and treatment", Geriatrics, vol. 58, No. 6, Jun. 2003, pp. 16-18, 24-30.

Julia B. Clark, et al., "The Diabetic Zucker Fatty Rat (41611)", Proceedings of the society for experimental Biology and Medicine, 1983, vol. 173, pp. 68-75.

Ohsawa, et al., "Effect of acute topical application of (+)-pentazocine on the mechanical allodynia in diabetic mice"Eur. J. Pharmacol., 2010, 641, pp. 49-53.

Otto et al., Pain Medicine, 2011, 12: 437-450, "Longitudinal Study of painful Diabetic Neuropathy in the Zucker Diabetic Fatty Rat Model of Type 2 Diabetes: Impaired Basal G-Protein Activity Appears to Underpin Marked Morphine Hyposensitivity at 6 Months".

Brussee et al, Diabetes, 2008, 57: 1664-1673, "Distal Degenerative Sensory Neuropathy in a Long-Term Type 2 Diabetes Rat Model".

Mega et al., Experimental Diabetes Research, Jan. 12, 2011, Diabetic Nephropathy Amelioration by a Low-Dose Sitagliptin in an Animal Model of Type 2 Diabetes (Zucker Diabetic Fatty Rat).

R. Quirion, et al., "A proposal for the classification of sigma binding sites", TiPS, vol. 13, 1992, pp. 85-86.

Gérard Said, "Diabetic Neuropathy", Proceedings advanced studies in Medicine, vol. 1, No. 11, Dec. 2001, pp. 457-459.

T. Schlegel, et al., "Responsiveness of C-fiber nociceptors to punctate force-controlled stimuli in isolated rat skin: lack of modulation by inflammatory mediators and flurbiprofen" Neuroscience Letters, vol. 361, 2004, pp. 163-167.

Sarah Wild, et al., "Global Prevalence of Diabetes", Diabetes Care, vol. 27, No. 5, May 2004, pp. 1047-1053.

A. A. F. Sima, et al., "A comparison of diabetic polyneuropathy in Type II diabetic BBZDR/Wor rats and in Type I diabetic BB/Wor rats", Diabetologia, vol. 43, 2000, pp. 786-793.

Anders A. F. Sima, "The heterogeneity of diabetic neuropathy", Frontiers in Bioscience, May 2008, pp. 4809-4816.

Yoshiaki Suzuki, et al., "Lowered response threshold and increased responsiveness to mechanical stimulation of cutaneous nociceptive fibers in streptozotocin-diabetic rat skin in vitro—correlates of mechanical allodynia and hyperalgesia observed in the early stage of diabetes", Neuroscience Research, vol. 43, 2002, pp. 171-178.

Loretta Vileikyte, et al., Psychological aspects of diabetic neuropathic foot complications: an overview, Diabetes/Metabolism Research and Reviews, vol. 20 (Suppl 1), pp. S13-S18.

Anthony P. Weetman, "Graves' hyperthyroidism: how long should antithyroid drug therapy be continued to achieve remission?", Nature Clinical Practice Endocrinology and Metabolism, vol. 2, No. 1, Jan. 2006, pp. 2-3.

C.L. Oltman, et al., "Vascular and neural dysfunction in Zucker diabetic fatty rats: a difficult condition to reverse", Diabetes, Obesity and Metabolism, vol. 10, 2008, pp. 64-74.

J. B. McGill, et al., "β-Blocker use and diabetes symptom score: results from the GEMINI study", Diabetes, Obesity and Metabolism, vol. 9, No. 3, May 2007, pp. 408-417.

C. L. Oltman, et al., Treatment of Zucker diabetic fatty rats with AVE7688 improves vascular and neural dysfunction, Diabetes, Obesity and Metabolism, vol. 11, No. 3, 2009, pp. 223-233.

JoséLuis Diaz, et al., "Selective Sigma-1 ($\sigma_1$) Receptor Antagonists: Emerging Target for the Treatment of Neuropathic Pain", Central Nervous System Agents in Medicinal Chemistry, Bentham Science Publishers Ltd., vol. 9, No. 3, Jan. 2009, pp. 172-183.

"Chemotherapy at home, pain and its treatment", Soins, Office De Publicite Generale, Paris, FR, (Sep. 1, 1989), No. 528, ISSN 0038-0814, pp. 17-20, XP009107313 [A] 1-16. * p. 19 *.

Aapro, M. et al., "Anticipatory Nausea and Vomiting", Support Care Cancer, 2005, vol. 13, pp. 117-121.

Abadias, M. et al. "Saftey, Tolerability and Pharmacokinetics of Single and Multiple Doses of a Novel Sigma-1 Receptor Antagonist in Three Randomized Phase I studies," British Journal of Clinical Pharmacology, 2012, 75:1, 103-117.

Botting, R.M.; Clinical Infectious Diseases, 2000, 31, S202-10.

Abraham, D.J., et al., "Burger's Medicinal Chemistry: Drug Discovery and Development" 7th edition, 8 volume set, 2010.

Abrams, P., et al., "The standardisation of terminology of lower urinary tract function: report from the standardisation sub-committee of the International Continence Society", Neurology and Urodynamics, 21, 2002, pp. 167-178.

Acta Obstetrica Gynecologica Japonica, 2000, vol. 52 (6), pp. 117-120.

Advokat, C., et al., "Selective antinociceptive effect of excitatory amino acid antagonists in intact and acute spinal rats," Pharmacology Biochemistry and Behavior 51(4):855-60 1995.

Alberts, D.S., et al., "Cisplatin-associated neurotoxicity: can it be prevented?" Anti-cancer Drugs, 1995, vol. 6, pp. 369-383.

Almerico, AM., "1-Methyi-3H-pyrazolo[1, 2-a]benzo[1, 2, 3, 4] tetrazin-3-ones: Design, synthesis and biological activity of new antitumor agents", Journal of Medicinal Chemistry, vol. 48, 2005, pp. 2859-2866.

(56) References Cited

OTHER PUBLICATIONS

Anderson, B. D. et al., "Preparation of Water-Soluble Compounds Through Salt Formation" The Practice of Medicinal Chemistry, Chapter 34, pp. 739-754.
Angst, M.S., et al., "Opioid-induced Hyperalgesia: A Qualitative Systematic Review," Anesthesiology. vol. 104 pp. 570-587 (2006).
Anonymous "Opioid-Induced hyperalgesia," http:/lweb.archive.org/web/20080712205531/http://en.wikipedia.org/wiki/Opioid-inducedhyperalgesia (retrieved Feb. 16, 2017).
Anton, E., "Delayed toxicity of cyclophosphamide on the bladder of DBA/2 and C57BL/6 female mouse," Int. J. Exp. Path., 83, 2002, pp. 47-53.
Arafa, et. al., Journal of Medicinal Chemistry, 2005, American Chemical Society, vol. 48, pp. 5480-5488.
Argyrioul, A.A., et al., "Bortezomib-induced peripheral neuropathy in multiple myeloma: a comprehensive review of the literature", Blood, 2008, vol. 112, No. 5, pp. 1593-1599.
Arthritis [online], [retrieved on Nov. 20, 2007]. Retrieved from the Internet, URL; http://www.nlm.nih.gov/medlineplus/ency/article/001243.htm>.
Asano, T., et al. Antinociception by epidural and systemic alpha(2)adrenoceptor agonists and their binding affinity in rat spinal cord and brain, *Anesth Anal g.* 2000; 90 (2): 400-407.
Baraldi, et al., "Ethyl 2, 4-Dioxoalkanoates as Starting Materials for a Convenient Route to 3(2H)Furanones and 3(2H) Furanimines", Tetrahedron, vol. 43, No. 1, pp. 235-242, 1987.
Baraldi, et al., "Ethyl 5-Substituted-3-Isoxazolecarboxylates as Starting Materials for a Convenient Route to 3(2H) Furanones and 3(2H)Iminofuranes", Tetrahedron Lett., 25(38), pp. 4313-4316; 1984.
Barnes, J.M. et al., "Reserpine, Para-Chlorophenylalanine and Fenfluramine Antagonise Cisplatin-Induced Emesis in the Ferret", Neuropharmacology, 1988, vol. 27, No. 8, pp. 783-790.
Batson, et al., "a-Hydroxy Cyclopentenones from a-Diketones", Organic Letters, vol. 7, No. 13, pp. 2771-2774, 2005.
Beaudegnies, R., et al. "Design and synthesis of novel spirocyclopropyl cyclohexane-1,3-diones and -1,3,5-triones for their incorporation into potent HPPD inhibitors", Tetrahedron Letters, 2010, vol. 51, pp. 2741-2744.
Bennett, G. J. "Pathophysiology and Animal Models of Cancer-Related Painful Peripheral Neuropathy", The Oncologist, 2010, 15 (suppl2), pp. 9-12.
Berge, S.M. et al., "Pharmaceutical Salts," Journal of Pharmaceutical Sciences, 1977, vol. 66, No. 1, pp. 1-19.
Bon, K., et al., "Characterization of cyclophosphamide cystitis, a model of visceral and referred pain, in the mouse: species and strain differences.", J UROL., (2003), vol. 170, No. 3, pp. 1008-1012.
Wickham, "Chemotherapy-Induced Peripheral Neuropathy: A Review and Implications for Oncology Nursing Practice" (2007) Clinical Journal of Oncology Nursing, vol. 11, No. 3, pp. 361-376.
Bowen W. D., Pharmaceutica *Acta Helvetiae*;2000; 74:211-218.
Brammer et al. in European Journal of Pharmacology, 553, 141-145 (2006).
Brennan, T.J., et al., "Characterization of a rat model of incisional pain", Pain, 1996, vol. 64, pp. 493-501.
Cobos, E. J., et al., Pharmacology and therapeutic potential of Sigma(1) receptor ligands. *Curr. Neuropharmacol.* 2008; 6, 344-366.
Bryans, J.S., et al., "3-substituted GABA analogs with central nervous system activity: a review," Med Res Rev, 19, 1999, pp. 149-177.
Bryans, J.S., et al., "Identification of novel ligands for the gabapentin binding site on the alpha-2-delta subunit of a calcium channel and their evaluation as anticonvulsant agents", J. Med. Chern. 41, 1998, pp. 1838-1845.
Bryant et al., Opioids and addiction: Emerging pharmaceutical strategies for reducing reward and opponent processes, Clinical Neuroscience Research, 2005, 5, pp. 103-115.

Buerkle, H., Yaksh, T. L. Pharmacological evidence for different alpha 2-adrenergic receptor sites mediating analgesia and sedation in the rat, *Br J Anaesth.* 1998; 81 (2): 208-215.
Bura, S.A. et al., "Evaluation of The Effect of The Selective Sigma-1 Receptor Antagonist SIRA in Neuropathic Pain Using An Operant Model", Eur J. Pain Supplements 2010, vol. 4, p. 49 (Abstract Only).
Buvanendran, A., et al. "Characterization of a New Animal Model for Evaluation of Persistent Postthoracotomy Pain", Anesth Analg, 2004, vol. 99, pp. 1453-60.
Cancer [online], [retrieved on Jul. 6, 2007]. Retrieved from the Internet, URL; http://www.nim.nih.gov/medlineplus/cancer.html>.
Cancer and Metastasis Reviews, 17(1), 91-106, 1998.
Cao, J., et al., "Dual Probes for the Dopamine Transporter and sigma1 Receptors: Novel Piperazinyl Alkyl-bis(4-ftuorophenyl)amine Analogues as Potential Cocaine-Abuse Therapeutic Agents", J. MED. CHEM, No. 13, Mar. 20, 1946, pp. 2589-2598.
Carlsson, et al., "Interaction of pentobarbital and morphine in the tail-ftick test performed on rates: synergism at the spinal and antagonism at the supraspinal level", NeuroSci. Lett.; 1986; 71; pp. 356-360.
Carrle, et al., Int Orthopaedics vol. 30, pase 445-451. publication year: 2006.
Carter, N., et al., "Duloxetine: a review of its use in the treatment of generalized anxiety disorder.", CNS Drugs 2009, (2009), vol. 23, No. 6, ISSN 1172-7047, pp. 523-541, ISSN: 1172-7047.
Case 07 "Joint Pain and Muscle Pain", Nurse Beans—Smart Nurse, Nov. 2007, vol. 9, No. II, pp. 1238-1239.
Celerier, et al., "Progressive Enhancement of Delayed Hyperalgesia Induced by Repeated Heroin Administration: A Sensitization Process," The Journal of Neuroscience. vol. 21, No. 11 pp. 4074-4080 (2001).
Cepeda, MS, "Comparison of Morphine, ketorolac, and their combination for postoperative pain: results form a large, randomized, double-blind trial", anesthesiology, 2005, vol. I03, No. 6, pp. I225-I232.
Cersosimo, R.J., "Oxaliplatin-Associated Neuropathy: A Review", The Annals of Pharmacotherapy, 20051 vol. 39 pp. 128-135.
Chaplan S. R., et al., "Quantitative assessment of tactile allodynia in the rat paw", J. Neurosci. Methods, (1994), vol. 53, pp. 55-63.
Chaudhry, V., et al., "Bortezomib and thalidomide-induced subacute demyelinating polyneuropathy," Clinical Neurophysiology, 2009, vol. 120, p. ell.
Chaudhry, V., et al., "Peripheral Neuropathy from Taxol and Cisplatin Combination Chemotherapy: Clinical and Electrophysiological Studies", Annals of Neurology, 1994, vol. 35, No. 3, pp. 304-311.
Chen, et al., Modern Bone Science, Modern Orthopaedics, "14.2.2 Drug Analgesia," p. 164, 2010, including English translation.
Chen, S.R., et al., "Synergistic Effect between Intrathecal Non-NMDA Antagonist and Gabapentin on Allodynia Induced by Spinal Nerve Ligation in Rats", Anesthesiology, 2000, vol. 92, pp. 500-506.
Díaz, J.L., et al., "Synthesis and Biological Evaluation of the 1-Arylpyrazole Class of sigma 1 Receptor Antagonists: Identification of 4-{2-[5-Methyl-1-(naphthalen-2-yl)-1 H-pyrazol-3-yloxy]ethyl}morpholine (S1RA, E-52862)", Journal of Medicinal Chemistry, (Oct. 11, 2012), vol. 55, No. 19, pp. 8211-8224.
Cherny, N., "Opioids and The Management of Cancer Pain", Eur. J. Cancer Supplement 2005, vol. 3, pp. 61-75.
Chichenkov, O.N. et al., "Effect of haloperidol on the analgesic activity of intracisternally and intrathecally injected opiate agonists," Farmakologiya I Toksikologiya, (1985), vol. 48. 48, No. 4, pp. 58-61.
Chien, C., et al., "Sigma antagonists potentiate opioid analgesia in rats," Neuroscience Letters, vol. 190, No. 2, 1995, pp. 137-139.
Chien, et al., "Selective Antagonism of Opioid Analgesia by a Sigma System," J. Pharmacol. Exp. Ther.; 1994; 271; pp. 1583-1590.
Cited ref STN serach abstract JP1 0055048.
Dugowson, et al.; Phys. Med. Rehabil. Clin. N. Arn. 2006, 17, 347-354.

(56) References Cited

OTHER PUBLICATIONS

Consilium MedSigma-receptors: new potentials of the treatment of depressions. Consilium Medicumicum 2012, vol. 14, No. 2 (found in the Internet: URL<new.Consiliummedicum.com/magazines/cm/medicum/article/21505, paragraphs 4-8).
Final Office Action dated Nov. 29, 2007 in related priority application U.S. Appl. No. 10/978,250.
Final Office Action dated Oct. 20, 2008 in related priority application U.S. Appl. No. 10/978,250.
Non-Final Office Action dated Apr. 16, 2008 in related priority application U.S. Appl. No. 10/978,250.
Non-Final Office Action dated Jun. 14, 2007 in related priority application U.S. Appl. No. 10/978,250.
Requirement for Restriction/Election dated Apr. 5, 2007 in related priority application U.S. Appl. No. 10/978,250.
Coxon, et al., "Acid-catalysed Rearrangements of trans- and cis-1-Acetoxy-3,4-epoxypentane and 1-Acetoxy-4,5-epoxyhexane", J_Chem_Soc_Chem_Commun., 8, pp. 261-262, 1973.
Crawford, K.W. et al., "Sigma-2 Receptor Agonists Activate a Novel Apoptotic Pathway and Potentiate Antineoplastic Drugs in Breast Tumor cell Lines1," Cancer Research, 2002, vol. 62, pp. 313-322.
D'Amour, F. E. and Smith, D. L. A method for determining the loss of pain sensation, *J. Pharmacal. Exp. Ther.* 1941; 72:74-79.
Dani, et al. (2007) The local antinociceptive effects of paracetamol in neuropathic pain are mediated by cannabinoid receptors. European Journal of Pharmacology 573(1-3): 214-215.
Danziger, et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London. Series B, Biological Sciences, vol. 236, No. 1283, pp. 101-113.
Herndon, et al.; Pharmacotherapy, 2008, 28(6), 788-805.
Dapeng Li "The Role of Glial Cells in . . . Pain", Thesis of Huazhong, University of Science and Technology, 2006, p. 24; Publication Date: Feb. 19, 2008.
Database WPI Week 200451 Thomson Scientific, London, GB; AN 2004-529624-& JP 2004 196678 A (DAINIPPON PHARM CO LTD) Jul. 15, 2004 (Jul. 15, 2004).
Dauben, W., et al., "Organic Reactions at High Pressure Preparation of Wittig Phosphonium Salts at Ambient Temperature", J. Org_Chern., 1984, vol. 49, pp. 4293-4295.
Davies, A., et al., "Functional biology of the alpha-2-delta subunits of voltage-gated calcium channels," trends in Pharmacological Sciences, vol. 28, No. 5, 2007, pp. 220-228.
DeHaven-Hudkins, et al., "Characterization of the binding of [H](+)-pentazocine to σ recognition sites in guinea pig brain," European Journal of Pharmacology—Molecular Pharmacology Section, 1992, vol. 227, pp. 371-378.
Dewar, "Diethyl-[3-(5-methyl-1-phenyl-1H-pyrazol-3-yl)-propyl]amine", Database Beilstein, Beilstein Institute for Organic Chemistry, Frankfurt-Main, DE, Database accession No. 213356, XP002605612 [X] 1-3,5,6,9. * the whole document *.
Dewar, M. J. S., "Attempts to find new Antimalarials. Part XXI", Journal Of The Chemical Society, (1944), pp. 615-619.
Dias, V. C., et al., Clinical experience with transdermal clonidine in African-American and Hispanic-American patients with hypertension: evaluation from a 12-week prospective, open-label clinical trial in community-based clinics, Am J Ther. 1999; 6 (1): 19-24.
Hinz et al., FASEB Journal, 2007, 7, 2343-2351.
Dixon, W. J., "Efficient analysis of experimental observations", Ann. Rev. Pharmacal. Toxicol., 20,1980, pp. 441-462.
Dmitrieva, N., et al., "The role of nerve growth factor in a model of visceral inflammation", Neuroscience, vol. 78, No. 2, 1997, pp. 449-459.
Dosen-Micovic, et. al., Bioorganic and Medicinal Chemistry, 2006, Elsevier, vol. 14, pp. 2887-2895.
Dougherty, P.M., et al. "Taxol-induced sensory disturbance is characterized by preferential impairment of myelinated fiber function in cancer patients", Pain, 2004, vol. 109, pp. 132-142.
Drug encyclopedia M., RLS 2001, pp. 572-573, articles "Morphine", "Morphine Sulfate".
Du, J., et al. "Kainate-induced Excitation and Sensitization of Nociceptors in Normal and Inflamed Rat Glabrous Skin", Neuroscience, 2006, vol. 137, pp. 999-1013.
Dukic-Ott, A. "Production of pellets via extrusion spheronisation without the incorporation of microcrystalline cellulose: A critical review," European Journal of Pharmaceutics and Biopharmaceutics, 2009, vol. 71, pp. 38-46.
Dunlap, B., et al., "Chemotherapy-Induced Peripheral Neuropathy Measurement", The Journal Of Supportive Oncology, 2006, vol. 4, 8, pp.
Dworkin R.H., "An Overview of Neuropathic Pain: Syndromes, Symptoms, Signs, and Several Mechanisms," The Clinical Journal of Pain 2002, vol. 18, pp. 343-349.
Dworkin, R.H. et a., "Recommendations for !he Pharmacological Management of Neuropathic Pain: Literature Update", Mayo Clin. Proc., 2010, 85(3)(Suppl), S3-S14.
Effenberger, F., et al., Chern. Ber., 102(10), 3260-3267, 1969.
Eghbaldar, et al., "Substances aromatisantes separation chirale par chromatographie gazeuse" Parfums, Cosmetiques, Aromes, 104, pp. 71-78, 1992.
Eisenach, J. C., et al., Intrathecal, but not intravenous, clonidine reduces experimental thermal or capsaicin-induced pain and hyperalgesia in normal volunteers; *Anesth Analg*; 1998; 87: 591-596.
Entrena, J.M., et al., "Sigma-I receptors are essential for capsaicin-induced mechanical hypersensitivity: Studies with selective sigma-1 ligands and sigma-1 knockout mice", PAIN, (2009), vol. 143, pp. 252-61.
Epilepsy [online], [retrieved on Nov. 20, 2007]. Retrieved from the Internet, URL; http://www.nim.nih.gov/medlineplus/ency/article/000694.htm>.
Epstein, et al., "Oral Doxepin Rinse: The Analgesic Effect and Duration of Pain Reduction in Patients with Oral Mucositis Due to Cancer Therapy" (2006) Pain Medicine, vol. 103, No. 2, pp. 465-470.
Epstein, et al., "Oral topical doxepin rinse: analgesic effect in patients with oral mucosal pain due to cancer or cancer therapy" (2001) Oral Oncology, 37:632-637.
Falk et al. "Pain and Nociception: Mechanisms of Cancer-Induced Bone Pain", Journal Clinical Oncology, 2014, vol. 32, pp. 1647-1654.
Field, M.J., et al., "Identification of the alpha-2-delta-1 subunit of voltage-dependent calcium channels as a molecular target for pain mediating the analgesic actions of pregabalin", PNAS, vol. 103, No. 46, Nov. 14, 2006, pp. 17537-17542.
Finnerup, N.B., et al. "The evidence for pharmacological treatment of neuropathic pain", Pain, 2010, vol. 150, pp. 573-581.
Forsyth, P.A., et al., "Prospective study of paclitaxel-induced peripheral neuropathy with quantitative sensory testing", Journal of Neuro-Oncology, 1997, vol. 35, pp. 47-53.
Maurice, T., Su, T. P., The pharmacology ofSigma-1receptors. *Pharmacal. Ther.* 2009; 124, 195-206.
Gabriel, A.F., Preoperative housing in an enriched environment significantly reduces the duration of post-operative pain in a rat model of knee inflammation, Neurosci. Lett. 2010, vol. 469, No. 2, pp. 219-232.
Gauchan, P., et al., "Mechanical Allodynia Induced by Pacli taxel, oxaliplatin and Vincristine: Different Effectiveness of Gabapentin and Different Expression of Voltage-Dependent Calcium Channel a26-1 subunit", Biol. Phann. Bull., 2009, vol. 32, No. 4 *f* pp. 732-734.
Gentili, M., et al., Intra-articular morphine and clonidine produce comparable analgesia but the combination is not more effective, *Br J Anaesth.* 1997; 79 (5): 660-661.
Glass et al., "Evaluation of pentamorphone in humans: a new potent opiate," Anesth. Analg. Mar. 1989, 68(3) 302-7.
Goblirsch, M.J., et al., "Biology of Bone Cancer Pain," Clin. Cancer Res. 2006, vol. 12 (20 Suppl.), pp. 6231s-6235s.
Goodman, et al., "The Pharmacological Basis of Therapeutics", 8th Ed.; 13-18, 1992.

(56) References Cited

OTHER PUBLICATIONS

Gordois, A., et al., "The Health Care Costs of Diabetic Peripheral Neuropathy in the U.S.", Diabetes Care, vol. 26, No. 6, Jun. 2003, pp. 1790-1795.
Gordon, A.N., et al., "Phase 1 Dose Escalation of Paclitaxel in Patients with Advanced Ovarian Cancer Receiving Cisplatin: Rapid Development of Neurotoxicity is Dose-Limiting", Journal of Clinical Oncology, 1997, vol. 15, No. 5, pp. 1965-1973.
Gotub et al., "Molecular Classification of Cancer: Class Discovery and Class Prediction by Gene Expression Monitoring," Science, 286: 531-537, 1999.
Grahame-Smith, D.G., et al., Oxford textbook on clinical pharmacology and drug therapy M., "Meditsina", 2000, pp. 658-661, Chapter "Narcotic analgesics".
Gralla et al. in Annals of Internal Medicine 95(4), 414-420 (1981).
Grover, S., et al., "Role of inflammation in bladder function and interstitial cystitis", Therapeutic Advances in Urology, 3(1), 2011, pp. 19-33.
Grunberg, S, M., et al., "Incidence of Chemotherapy-Induced Nausea and Emesis after Modern Antiemetics," Cancer, 2004, vol. 100, pp. 2261-2268.
Guignard, et al., "Acute Opioid Tolerance: Intraoperative RemifentanilIncreases Postoperative Pain and Morphine Requirement," Anesthesiology, vol. 93 pp. 409-417 (2000).
Guitart, X., et al., "Sigma receptors biology and therapeutic potential", Psychophamacology, 2004, vol. 17 4, pp. 301-319.
Haleblian, "Characterization of Habits and Crystalline Modification of Solids and Their Pharmaceutical Applications," Journal of Pharmaceutical Sciences, vol. 64, No. 8 pp. 1269-1288 (1975).
Hall, J. E., Uhrich, T. D., Ebert, T. J. Sedative, analgesic and cognitive effects of clonidine infusions in humans, *Br J Anaesth.* 2001; 86 (1): 5-11.
Hammack, et al., "Phase III evaluation of nortriptyline for alleviation of symptoms of cis-platinum-induced peripheral neuropathy" (2002) Pain, 98:195-203.
Hancock, et al., "Characteristics and Significance of the Amorphous State in Phamnaceutical Systems," Journal of Phamnaceutical Sciences, vol. 86, No. 1 pp. 1-12 (1997).
Hanner, et al., "Purification, molecular cloning, and expression of the mammalian sigma1-binding site," Proc. Natl. Acad. Sci., USA, Jul. 1996, vol. 93, pp. 8072-8077.
Hanno, Philip, "International Consultation on IC—Rome, Sep. 2004/Forging an interenational consensus: progress in painful bladder syndrome/interstitial cystitis", Int Urogynocol J, 16, 2005, pp. S2-S34.
Harden, N., et al., "Unmet Needs in the Management of Neuropathic Pain", Journal of Pain and Symptom Management, 2003, 25, 5S, S12-S17.
Hartwig, J., "Synthesis, Structure, and Reactivity of a Palladium Hydrazonato Complex: A New Type of Reductive Elimination Reaction to FormC-N Bonds and Catalytic Arylation of Benzophenone Hydrazone", Agnew. Chern. Int. Ed., 1998, vol. 37, No. 15, pp. 2090-2093.
Hayashi, T., et al., "Sigma-1 receptor ligands: potential in the treatment of neuropsychiatric disorders," CNS Drugs. 2004;18(5):269-84.
Hecht, J. R.' et al., "Prolonged Nausea and Vomiting after High Dose Chemotherapy and Autologous Peripheral Stem Cell Transplantation in the Treatment of High Risk Breast Carcinorrta," Cancer, 19971 vol. 7 9' pp. 1698-1702.
Herrstedt, J., et al., \'Acute emesis moderately emetogenic chemoc. herapy, Support Care Cancer, 2005, vol. 13, pp. 97-103.
Hesketh, M.' et al., "Proposal for classifying the Acute Emetogenicity of Cancer Chemotherapy", Journal of Clinical Oncology, 1997, vol. 15, pp. 103-109.
Hidaka, T., et al., W5-7 "A Basic Study of the Effect Peony Licorice Water on Paclitaxel-Induced Pain in Mice", Japan Academic Journal of Cancer Treatment, Sep. 2009, vol. 44, No. 2, p. 323 [inc. machine English language translation).

Hileman, G.A., et al., "Response surface optimization of high dose pellets by extrusion and spheronization," International Journal of Pharmaceutics, 1993, vol. 100, pp. 71-79.
Hiranita, et al., "Reinforcing effects of sigma-receptor agonists in rats trained to self-administer cocaine," J Pharmacol Exp Ther. Feb. 2010; 332(2):515-524 (2010).
Horner, et al., "Azo-aryle and Phenazine aus primaren Arylaminanionen durch Autoxydation", Chern. Be. 96, pp. 786-793, 1963.
Hsu, et al., Toxic. Appl. Pharmac., vol. 73, No. 3, p. 411-415, 1984.
Hudzik T. J., "Sigma Ligand-Induced Emesis in the Pigeon," Pharmacology Biochemistry & Behavior, 1991, 41(1), pp. 215-217.
Hudzik, T., et al., "o Receptor-mediated emetic response in pigeons: agonists, antagonists and modifiers", European Journal of Pharmacology, 1993, vol. 236, pp. 279-287.
IASP Classification of Chronic Pain, 2002, 2nd edition, pp. 201-213.
Isakov "The problem of pain in oncology", Russian Medicinal Journal, 2000, vol. 17, pp. 723-727.
Isomers [on-line], [retrieved on Mar. 11, 2007]. Retrieved from the Internet, URL; http://chemed.chem.purdue.edu/genchem/topicreview/bp/1organic/isomers.html>.
Izenwasser, S., et al "Characterization of kappa-opioid receptor binding in human insular cortex", Life Sciences, Pergamon Press, Oxford, GB, vol. 65, No. 9, Jul. 23, 1999, pp. 857-862.
Janicki, et al., "Detection of Antagonist Activity for Narcotic Analgesics in Mouse Hot-Plate Test" Pharmacol. Biochem. Behavior, 1979; 10(4); pp. 623-626.
Jordan, K., et al. "Chemotherapy-induced nausea and vomiting: current and new standards in the antiemetic prophylaxis and treatment," Eur J Cancer. Jan. 2005;41 (2):199-205.
Jover, I., et al., "Evaluation, by a Statistically Designed Experiment, of an Experimental Grade of Microcrystalline Cellulose, Avicel 955, as a Technology to Aid to Production of Pellets with High Drug Loading," Journal of Pharmaceutical Sciences, 1996, vol. 85, No. 71 pp. 700-705.
Kaiser, et al., *Neurotransmissions*; 1991; 7(1); 1-5.
Kautio, et al., "Amitriptyline in the Prevention of Chemotherapy-induced Neuropathic Symptoms" (2009) Anticancer Research, 29:2601-2606.
Kautio, et al., "Amitriptyline in the Treatment of Chemotherapy-Induced Neuropathic Symptoms" (2008) Journal of Pain and Symptom Management, 35(1):31-39.
Kawamata, M., et al. "Experimental incision-induced pain in human skin: effects of systemic lidocaine on flare formation and hyperalgesia", Pain, 2002, vol. 100, pp. 77-89.
Kehlet, H., et al. "Persistent Surgical Pain: Risk Factors and Prevention," Lancet, 2006, vol. 367; pp. 1618-1625.
Kehlet, H., et al. "PROSPECT: evidence-based, procedure-specific postoperative pain management", Best Practice Res Clin Anaesthesiol., 2007, vol. 21, pp. 149-159.
Kehlet, H., et al., "Anaesthesia, surgery, and challenges in postoperative recovery", Lancet 2003, vol. 362, pp. 1921-1928.
Kadiroglu, K.A., et al., "The effect of venlafaxine HCI on painful peripheral diabetic neuropathy in patients with type 2 diabetes mellitus.", Journal of Diabetes and Its Complications Jul.-Aug. 2008, (Jul. 2008), vol. 22, No. 4, ISSN 1873-460X, pp. 241-245, XP002721925 [Y] 1-17 * Venlafaxine HCI is effective in the treatment of peripheral diabetic neuropathic pain *.
Kenakin, A., Pharmacology Primer, The Evolving Pharmacology of GPCR's, 2006, pp. 27-60.
Kerba, et al. Oct. 2010, Journal of Clinical Oncology, vol. 28, No. 33, pp. 4892-4897.
Kest, et. al., Pharmacology Biochemistry, and Behavior, 1995, Pergamon, vol. 52, No. 1, pp. 175-178.
Khouzam, H. R., et al., "Remission of Cancer Chemotherapy-Induces Emesis During Antidepressant Therapy with Nefazodone", Psychosomatic Medicine, 1998, vol. 60, pp. 89-91.
Kim, et al., "Activation of the spinal sigma-1 receptor enhances NMDA- induced pain via PKC- and PKA-dependent phosphorylation of the NRI subunit in mice", Br. J. Pharmacal., 2008, vol. 154, pp. 1125-1134.
Kim, et al., Int Neurourol J.; Mar. 2016; 20(1); 13-17.

(56) References Cited

OTHER PUBLICATIONS

Kirchmair, R., et al., "Therapeutic Angiogenesis Inhibits or Rescues Chemotherapy-induced Peripheral Neuropathy: Taxol- and Thalidomide-induced Injury of Vasa Nervorum is Ameliorated by VEGF," Molecular Therapy, 2 DD7, vol. 151 No. 1, pp. 69-75.
Koralewski, p., et al., Effectiveness of cyproheptadine in the management of delayed vomiting after cisplatin-based chemotherapy and the assessment of the influence of cyproheptadine on quality of lifen, Chemotherapy Dept. Rydygier Memorial Hospital, Cracow, Poland, vol. 5, pp. 499-503.
Kranz, H., et al., "Drug Release from MCC- and carrageenan-based pellets: Experiment and theory," European Journal of Pharmaceutics and Biopharmaceutics, 2009, vol. 73, pp. 302-309.
Kuloor, et. al., Age and Aging, 2006, Oxford University Press, vol. 35, pp. 639-640.
Kunz, N. R., et al., "Diabetic neuropathic pain management with venlafaxine extended release", European Neuropsychopharmacology, Elsevier Science Publishers BV, Amsterdam, NL, vol. 10, ISSN 0924-977X, (Sep. 1, 2000), p. 389, (Sep. 1, 2000), XP027389705 [Y] 1-17. * Venlafaxine controlled release is effective in the treatment of pain *.
Kuruvilla et al., Arch Otolaryngol Head Neck Surg. Jan. 2009; 135(1): 101-105.
Romero, L., et al., J. Pharmacological properties of SIRA, a new Sigma-1 receptor antagonist that inhibits neuropathic pain and activity-induced spinal sensitization. *Br. J. Pharmacal.* 2012; doi: 10.1111/j.1476-5381.
LaBuda, et al., (2005) Pharmacological evaluation of the selective spinal nerve ligation model of neuroFathic pain in the rat. J. Neurosci. Methods 144 (2):175-181.
LaBudde, et al., "The Synthesis of the Mono- and Dihydroxy Derivatives of 1,2,5,6-Dibenzanthracene Excreted by the Rabbit and of Other Hydroxylated Dibenzanthracene Derivatives", J. Am. Chern. Soc., 80, pp. 1225-1236, 1958.
Laggner et al. "Discovery of High-Affinity Ligands of Sigma Receptor, ERG2, and Emopamil Binding Protein by Pharmacophore Modeling and Virtual Screening", J. Med. Chem., 2005, vol. 48, pp. 4754-4764.
Langa, et al., "Generation and phenotypic analysis of sigma receptor type I (σ1) knowckout mice," European Journal of Neuroscience, 2003, vol. 18, pp. 2188-2196.
Laird, J., et al., "Deficits in visceral pain and referred hyperalgesia in Nav1.8 (SNS/PN3)-null mice", The Journal of Neuroscience, 22(19), Oct. 1, 2002, pp. 8352-8356.
Lang, M., et al., "The Use of Polymer Heteronuclei for Crystalline Polymorph selection," Journal of the American Chemical Society, 2002, vol. 124, No. 50, pp. 14834-14835, SI-S2.
Lau, et al. (2010) Electroacupuncture versus celecoxib for neuropathic pain in rat SNL model. Neuroscience 170 (2): 655-661.
Le Bars, D., et al., Animal models of nociception. *Pharmacal. Rev.* 2001; 53, 597-652.
Lee, M. et al., "A Comprehensive Review of Opioid-Induced Hyperalgesia," Pain Physician. vol. 14 pp. 145-161 (2011).
Lee, S., et al., "Large-Scale Aspects of Salt Formation: Processing of Intermediates and Final Products", Handbook of Pharmaceutical Salts: Properties, Selection, and use, 2002, Chapter 8, pp. 191-192, 211-214, Chapter 12, 265-266, 282-283.
Levine, J.D. et al., "Desiperamide Enhances Opiate Postoperative Analgesia", Pain, 1986, vol. 27, pp. 45-49.
Li, et al., "Asymmetric Total Synthesis and Formal Total Synthesis of the Antitumor Sesquiterpenoid (+)-Eremantholide A", Organic Letters, vol. 9, No. 7, pp. 1267-1270, 2007.
Li, et at., "Synthesis and Structure-Antitumor Activity of 4,6-Diamino-1,2-Dihydro-2,2-Dimethyi-1-(Substituted Naphthyi-2)-1,3,5-Triazines", Chern. Res. Chinese Univ., 7(3), pp. 197-200, 1991.
Sakurada T., et al., Differential effects of intraplantar capsazepine and ruthenium red on capsaicin-induced desensitization in mice. Pharmacal Biochern Behav. Apr. 2003; 7 5 (1): 1 15-21.

Lippincott's Illustrated Review: Pharmacology, Richard Harvey, 5th, edition published by Wolters Kluwer "Gastrointestinal and Antiemetic Drugs", pp. 351-362.
Lowry, et al., "Protein measurement with the folin phenol reagent," J. Bio.Chem, 1951, vol. 193, pp. 265-275.
Luedtke, R. R., et al., "Neuroprotective effects of high affinity Sigma 1receptor selective compounds," Brain Res. Mar. 2, 2012;1441:17-26.
Luger N.M., et al., "Efficacy of systemic morphine suggests a fundarnen tal difference in the mechanisms that generate bone cancer vs. inflammatory pain", Pain 2002, vol. 99, pp. 397-406.
Luger, N.M., et al., "Bone Cancer Pain: From Model to Mechanism to Therapy", J. Pain and Symp. Manag. 2005, vol. 29 pp. 832-846.
Lytle, et al., "Effects of long-term corn consumption on brain serotonin and the response to electric shock," Science vol. 190, pp. 692-694 (1975).
Mantyh, "Bone cancer pain: From mechanism to therapy", Opin. Support. Palliat. Care, 2014, vol. 8, pp. 83-90.
Mao, J., "Opioid-induced abnormal pain sensitivity: implications in clinical opioid therapy," Pain. vol. 100 pp. 213-217 (2002).
Mar. 1, 2016 Fourth Office Action, issued in connection with Chinese Patent Application No. 201180065232.X, including English language translation.
Mar. 29, 2016 Office Action, issued in connection with Japanese Patent Application No. 2013- 541369, including English translation.
Marks, D.M., et al., "Serotonin-Norepinephrine reuptake inhibitors for pain control: Premise andpromise", Current Neuropharmacology, 2009, 7, pp. 331-336.
Maryanoff, B.E., et al., The Wittig Olefination Reaction and Modifications Involving Phosphoryl-Stabilized Carbanions. Stereochemistry, Mechanism, and Selected Synthetic Aspectsu, Chern. Rev., 1989, vol. 89, pp. 863-927.
Matsumoto RR1, Pouw B. Correlation between neuroleptic binding to sigma(1) and sigma(2) receptors and acute dystonic reactions. Eur J. Phamacol. Aug. 4, 2000;401(2):155-60.
Max, M.B., et al. "Endogenous Monoamine Analgesic Systems: Amitriptyline in Painful Diabetic Neuropathy", Anesth. Prog., 1987, vol. 34, pp. 113-127.
Telleria-Diaz, et al., Pain, 2010, 148, pp. 26-35.
Wilkes, G. "Peripheral Neuropathy Related to Chemotherapy", Seminars in Oncology Nursing, 2007, vol. 23, 3. pp. 162-173.
Mei, et al., "Receptor Modulation of Opioid Analgesia in the Mouse", J. Pharmacol Exp. Ther.; 2002; 300(4); pp. 1070-1074.
Mielke, S. et al., "Peripheral neuropathy: A persisting challenge in paclitaxel-based regimes"/European Journal of Cancer, 2006, vol. 42, pp. 24-30.
Ming, L.C., "Screening Polymorphic Forms of Drug Substances by Using Generalized Crystallization Techniques," May 2007 (English language Translation of Abstract).
Moncada A., et al., Effects of serine/threonine protein phosphatase inhibitors on morphine-induced antinociception in the tail flick test in mice. *Eur J Pharmacal*. 2003; Mar. 28; 465(1-2): 53-60.
Mosandl, et al., "Stereoisomeric Flavor Compounds XLIV: Enantioselective Analysis of Some Important Flavor Molecules", J. High Resol. Chromatog 13(9), pp. 660-662, 1990.
Mouedden, et al., "Pharmacological evaluation of opioid and nonopioid analgesics in a murine bone cancer model of pain", Pharm. Biochem. And Behavior, 2007, vol. 86, pp. 458-467.
Mueller, et al., "Some Derivatives of 7-Methoxy- and 10-Methoxybenzo (f) quinoline", J. Am. Chem. Soc., 66, pp. 860-862, 1944.
Mukerji, et al., "Addition of Nitrite Oxides to Olefins, Synthesis of Dihydrojasmone and Starting Material for Prostanoids. A Novel Route to Pyrroles", Tetrahedron, 39 (13) pp. 2231-2235, 1983.
Nakajima K., et al., An increase in spinal cord noradrenaline is a major contributor to the antihyperalgesic effect of antidepressants after peripheral nerve injury in the rat. *Pain*. 2012; 153(5): 990.
Nakazato A., et al., "Synthesis and SAR of 1-alkyl-2-phenylethylamine derivatives designed from N,Ndipropyl-4-methoxy- 3-(2-phenylethoxy) phenylethylamine to discover ?1ligands", J. Med. Chem., (1999), vol. 42, pp. 3965-3970.

(56) References Cited

OTHER PUBLICATIONS

Narujo, Hiroyuki et al., Cancer Pain Treatment—Clinical Oral Morphine Extended-Release Tablets (once/day)—5$^{th}$, Pharma Medical, 2007, including English language translation.

Nausea and Vomiting (PDQ) Health Professional Version: Prevention and Managemenl of Acute or Delayed Nausea and Vomiting (Emesis). National Cancer Institute. <http://www.cancer.gov/about-cancer/treatment/sideeffects/nausea/nausea-hp-pdq#sectIon/-66>.

Nieto, F. R., et al., "188 A New Selective Sigma-1 Receptor Antagonist (S1RA) Inhibits the Development and Expression of Neuropathic Pain Induced by Paclitaxel in Mice," European Journal of Pain Supplements, vol. 4, No. 1, 2010, p. 56.

Nieto, F.R., et al., "Tetrodotoxin inhibits the development and expression of neuropathic pain induced by paclitaxel in mice", Pain, 2008, vol. 137, pp. 520-531.

Niiyama, et al., "SB366791, a TRPVI antagonist, potentiates analgesic effects of systemic morphine in a murine model of bone cancer pain", Br. J. Anaesth., 2009, vol. 102, pp. 251-258.

Noda, et al., "A Neuroactive Steroid, Dehydroepiandrosterone Sulfate, Attenuates The Development of Morphine Dependence: An Association with Sigma1 Receptors," Neuroscience 2001 Abstract, Presentation No. 668.4, Nov. 2001.

Nomura, M., et al., "Studies on drug dependence (Rept. 322): Attenuation of morphine- and psychostimulants-induced place preference by sigma1 receptor agonist SA4503", Japanese Journal of Pharmacology, The Japanese Pharmacological Society, Kyoto, JP, vol. 79, No. suppl. 1, Jan. 1, 1999, p. 224P.

O'Brien, C. J., "Recycling the Waste: The Development of a Catalytic Witting Reaction", Agnew. Chern. Int. Ed. 2009, vol. 48, pp. 6836-6839.

Office Action and Search Report corresponding to Taiwanese Patent Application No. 100127236 (Translation) [undated].

Office Action dated Mar. 18, 2013 in connection with Russian Patent Application No. 2010138634, filed Feb. 17, 2009.

Official Action corresponding to Japanese Patent Application No. 2013-523580, dated Mar. 31, 2015.

Wilson, S. G., "The heritability of antinociception: common pharmacogenetic mediation of five neurochemically distinct analgesics," J Pharmacal Exp Ther. 2003; 304 (2): 547-559.

Olivar, T., et al., "Cyclophosphamide cystitis in mice: behavioural characterisation and correlation with bladder inflammation", European Journal of Pain, 3, 1999, pp. 141-149.

Winkler, et al., "Synthesis of Highly Functionalized Furanones via Aldol Reaction of 3-Silyloxyfurans", Organic Letters, vol. 7, No. 3, pp. 387-389, 2005.

Wolf et al., Chemotherapy-induced peripheral neuropathy: Prevention and Treatment strategies, European Journal of Cancer, 2008,44,1507-1515.

Wong, H.Y., et al., Pentarnorphone for Management of Postoperative Pain. Anesth Analg. 1991; 72:656-60.

O'Neill, J., et al., Unravelling the mystery of capsaicin: a tool to understand and treat pain. Pharrnacol Rev. Oct. 2012;64(4):939-71.

Ongioco, C. D., et al., Alpha2-adrenergic receptors in human dorsal root ganglia: predominance of alpha2b and alpha2c subtype mRNSs, Anesthesiology 2000; 92 (4): 968-976.

Osipova, N.A., "Tramadol (Tramal) in the Treatment of Acute and Chronic Pain Syndromes," Russky Meditsinsky Zhurnal (Russian Medicinal Journal), Feb. 25, 2003, No. 4, Sections: Pulmonology: Selected Lectures for Family Physicians (Retrieved from the Internet: URL<rmj.ru/number_36.htm.

Wu, et al., Regulatory Perspectives of Type II Prodrug Development and Time-Dependent Toxicity Management: Nonclinical Pharm/Tox Analysis and the Role of Comparative Toxicology, Toxicology, 236: 1-6, 2007.

Owens, N.J. et al., "Antiemetic efficacy of prochlorperazine, haloperidol, and droperidol in cisplatin-induced emesis", Clinical Pharmacy, 1984, vol. 3, pp. 168-170.

Pacharinsak, C., et al., "Animal Models of Cancer Pain", Comparative Medicine, 2008, vol. 58, No. 3, pp. 220-233.

Paice, J. A., "Clinical Challenges: Chemotherapy-induced Peripheral Neuropathy", Seminars in Oncology Nursing, 2009, vol. 25, N. 2, Suppl 1, pp. S8-S19.

Palmer, J. L., and Fisch, M. J., "Association Between Symptoms Distress and Survival in Outpatients Seen in a Palliative Care Caner Center", Journal of Pain and Symptom Management, 2005, vol. 29, No. 6, pp. 565-571.

Paquette et al. in Psychopharmacology (Berlin) 204(4):743-754 (2009).

Park, S.B. et al. "Mechanisms Underlying Chemotherapy-Induced Neurotoxicity and the Potential for Neuroprotective Strategies", Current Medicinal Chemistry, 2008, vol. 15, pp. 3081-3094.

Perret, D., et al., "Targeting voltage-gated calcium channels for neuropathic pain management", Neurotherapeutics: The Journal of the American Society for Experimental NeuroTherapeutics, vol. 6, Oct. 2009, pp. 679-692.

Petrie, C., et al., "A Novel Biotinylated Adenylate Analogue Derived from Pyrazolou3,4-D 3/4 Pyrimidine for Labeling DNA Probes" Bioconjugate Chemistry, ACS, Washington, DC, US LNKD- DOI:10.1021/BC00012A011, val. 2, No. 6, Nov. 1, 1991 (Nov. 1, 1991), pp. 441-446, XP0005727891SSN: 1043-1802.

Pirim, A., et al., "Addition of ketamine infusion to patient controlled analgesia with intravenous morphine after abdominal hysterectomy" Agri Jan. 2006; 18(1):52-8 Abstract.

Polomano, R.C., et al., "Chemotherapy-evoked Painful Peripheral Neuropathy", Pain Medicine, 2001, vol. 2, No. 1, pp. 8-14.

Polomano, R.C., et al., "Pain and neuropathy in cancer survivors: Surgery, radiation, and chemotherapy can cause pain; research could improve its detection and treatment", Cancer Nursing, Lippincott-Raven Pub., Hagerstown, MD, US, (Mar. 1, 2006), vol. 29, No. 2, suppl, ISSN 0162-220X, pp. 39-47, XP009107315 [A] 1-16 * p. 41, col. R, paragraph 2 * * p. 42, col. R, paragraph 2 *.

Wunsch, et al., Journal Med. Chem. vol. 55, No. 19, pp. 8209-8210, 2012.

Postma, T.J., et al., "Paclitaxel-induced neuropathy," Annals of Oncology, 1995, vol. 6, pp. 489-494.

Price, et al., J. Am. Chem. Soc., (2005), vol. 127, p. 5512.

Prodrug [online], [retrieved on Mar. 11, 2007. Retrieved from the Internet, URL; http://en.wikipedia.org/wiki/Prodrug>.

Puente, B., et al., "Sigma-1 receptors regulate activity-21 induced spinal sensitization and neuropathic pain after peripheral nerve injury", Pain, 2009, vol. 145, pp. 294-303.

Puskas, F., et al., Intrathecal clonidine and severe hypotension after cardiopulmonary bypass, Anesth Analg. 2003; 97 (5): 1251-1253.

Quasthoff, S., et al., "Chemotherapy-induced peripheral neuropathy," J Neural., 2002, vol. 249, pp. 9-17.

Radesca, et al., "Synthesis and Receptor Binding of Enantimeric N-Substituted cis-N-[2(3,4 Dishlorophenyl)ethyl]-2-(1-pyrrolidinyl)cyclohexylamines as High-Affinity σReceptor Ligands," J. Med. Chem., 1991, vol. 34, pp. 3058-3065.

Rao, R.D., et al., "Efficacy of Lamotrigine in the Management of Chemotherapy-induced Peripheral Neuropathy placebo-controlled trial, N01C3", Cancer; 2008, 112(12), 2802-2808.

Raynov, J., "Antiemetics: Side effects and reactions", Archive of Oncology, 2001, vol. 9, No. 3, pp. 151-153.

Receveur, Jean-Marie, et al., "Synthesis and biological evaluation of conformationally restricted gabapentin analogues", Bioorganic & Medicinal Chemistry Letters, 9, 1999, pp. 2329-2334.

Reuben, S. S., et al., "Evaluation of efficacy of the perioperative administration of venlafaxine XR in the prevention of postrnastectorny pain syndrome", Journal of Pain and Symptom Management, Feb. 2004, vol. 27, No. 2, pp. 133-139.

Rodriguez-Spong, B., et al., "General principles of pharmaceutical solid polymorphism: a supramolecular Perspective," Advanced Drug Delivery Reviews, vol. 56 (2004) pp. 241-274.

Roh, D., et al., "Intrathecal Injection of the 01 Receptor Antagonist BD1047 Blocks Both Mechanical Allodynia and Increases in Spinal NR1 Expression during the Induction Phase of Rodent Neuropathic Pain", Anesthesiology, 2008, vol. 109, No. 5, pp. 879-889.

Roila, F., et al., "Delayed emesis: moderately emetogenic chemotherapy", Support Care Cancer, 2005, vol. 13, pp. 104-108.

Roos, et al., Radiotherapy and Oncology, 2003, vol. 67, pp. 207-212.

(56) References Cited

OTHER PUBLICATIONS

Rossiter, et al., "Copper (H)-Mediated Arylation with Aryl Boronic Acids for the N-Derivatization ofPyrazole Libraries," J. Comb. Chern., 2004, vol. 6, pp. 385-390, published on web Feb. 5, 2004.
Rouleau, A., et al., "Anti-inflammatory and antinociceptive properites of BP 2-94, a histamine H3-receptor agonist prodrug", The Journal of Pharmacology and Experimental Therapeutics, vol. 295, No. 1, 2000, pp. 219-225.
Rowinsky, E.K. et al., "Phase I and Pharmacologic Study of Paclitaxel and Cisplatin with Granulocyte Colony-25 Stimulating Factor: Neuromuscular Toxicity is Dose-Limiting", Journal of Clinical Oncology, 1993, vol. 11, No. 10, pp. 2010-2020.
Rowinsky, E.K., et al., "Clinical Toxicities Encountered 24 with Paclitaxel (TAXOL)", Seminars in Oncology, 1993, vol. 20, No. 4, suppl. 3, pp. 1-15.
Sabetkasaie, M., et al., "Clonidine and guanfacine-induced antinociception in visceral pain: possible role of alpha2/12 binding sites", European Journal of Pharmacology, Elsevier Science, NL, (Oct. 6, 2004), vol. 501, No. 1-3, doi:10.1016/J.EJPHAR.2004.08. 010, ISSN: 0014-2999, pp. 17182-17187.
Saha, et al., "Spinal Mitogen-Activated Protein Kinase Phosphatase (MKP-3) Is Necessary for the Normal Resolution of Mechanical Allodynia in a Mouse Model of Acute Postoperative Pain", J. Neurosci., 2013, vol. 43, pp. 17182-17187.
Xiaoping, et al., "Involvement of the spinal NMDA receptor/PKCy signaling 12 pathway in the development of bone cancer pain", Brain Research, 2010, vol. 1335, pp. 83-90.
Xu, J. et al., Identification of the PGRMCI protein complex as the putativP. sigrna-2 receptor binding site. Nat Comnun. Jul. 5, 2011; 2:380.
Sampson, C., et al., "Effects of imidazoline I2 receptor ligands on acute nociception in rats." Neuroreport Jan. 25, 2012, (Jan. 25, 2012), vol. 23, No. 2, ISSN 1473-558X, pp. 73-77, * See abstract: imidazoline I2 receptor ligands have antinociceptic effect in acute pain *.
Samso, E., et al., Comparative assessment of the anaesthetic and analgesic effects of intramuscular and epidural clonidine in humans, Can J Anaesth. 1996; 43 (12): 1195-1202.
Sanchez-Fernandez, C., et al., "Potentiation of morphine-induced mechanical antinociception by sigma-1 receptor inhibition: role of peripheral sigma-1 receptors", Neuropharmacology, 70, 2013, pp. 348-358.
Sandford, M., et al., Pain Physician 2009; 12:679-684.
Sant et al., "The mast cell in interstitial cystitis: role in pathophysiology and pathogenesis," Urology, 69, Suppl 4A, 2007, pp. 34-40.
Schetz et al. in Brain Research 1181 (2007) 1-9.
Schiff, et al., Nature vol. 277 pp. 665-667. Publication date: Feb. 22, 1979.
Yaksh, T. L., Pharmacology of spinal adrenergic systems which modulate spinal nociceptive processing. *Pharmacal Biochem Behav.* '1985; 22(5): 845-58.
Schoeffter, et al., "Functional, endogenously expressed 5-hydroxytryptamine 5-ht7 receptors in human vascular smooth muscle cells," British Journal of Pharmacology, 1996, vol. 117, pp. 993-994.
Schreiber, S., et al., "The antinociceptive effect of venlafaxine in mice is mediated through opioid and adrenergic mechanisms", Neuroscience Letters, Limerick, IE, (Jan. 1, 1999), vol. 273, doi:10. 1016/S0304-3940(99)00627-8, ISSN 0304-3940, pp. 85-88, XP003009174 [Y] 1-17* Venlafaxine has antinociceptive effects and is effective for treating pain.*
Seigel, L.J., et al., The Control of Chemotherapy-Induced Emesis, Ann Intern Med. 1981;95(3):352-359.
Selwood, D. L., et al. Synthesis and Biological Evaluation of Novel Pyrazoles and Indazoles as Activators of the Nitric Oxide Receptor, Soluble Guanylate Cyclase, J. Med. Chern, 2001, vol. 44, pp. 78-93.
Sevcik, M.A., et al., "Jlnti-NGF therapy profoundly reduces bone cancer pain and the accompanying increase in markers of peripheral and central sensitization", Pain 2005, vol. 115, pp. 128-141.
Shaw, et al., Proc. Soc. Exp. Biol. Med., (1983), vol. 173, No. 1, pp. 68-75.
Shen, D.M., et al., "Versatile and Efficient Solid-Phase Syntheses of Pyrazoles and Isoxazoles", Organic Letters, 2000, vol. 2, No. 18, pp. 2789-2792.
Shimizu, I., et al., "Effects of AH-9700, (+)-pentazocine, DTG and oxybutynin on micturition in anesthetized rats with acetone-induced cystitis", Life Sciences 69, 2001, pp. 1691-1697.
Shimoyama, E., et al., Integrative Medicine you Need to know now "Cancer and Integrative Medicine Palliative Medicine", Modern Physician, Nov. 2008, vol. 28, No. 11, pp. 1605-1607 [inc. machine English language translation].
Shu, et al., "Parameter Effects on the Thermal Reaction of Cystine and 2,5-Dimethyl-4-hydroxy-3(2H)-furanone", ACS Symposium Letters, 409, pp. 229-241, 1989.
Shvidenko, K.V., et al., "Recyclization Reactions of 2-(1-Benzoylpyrrolidin- 2-Ylidene)Malononitrile", 2010, vol. 46, No. 1, pp. 56-60.
Siau, C., et al., "Dysregulation of Cellular Calcitt.rn Homeostasis in Chemotherapy-Evoked Painful Peripheral Neuropathy", Anest:h Analg., 2006, 102(5), pp. 1485-1490.
Sierralta, F., et al., Alpha-Adrenoceptor and opioid receptor modulation of clonidine-induced antinociception, Br J Pharmacal. 1996; 119 (3): 551-554.
Silvererman, M., "Opioid Induced Hyperalgesia: Clinical Implications for the Pain Practitioner," Pain Physician. vol. 12, pp. 679-684 (2009).
Silvey et al. in Journal of Clinical Oncology 6(9), 1397-1400 (1988) (Abstract).
Yasuda, M., et al., "Mast Cell Stabilization Promotes Antinociceptive Effects in a Mouse Model of Postoperative Pain," J. Pain Res., 2013, vol. 6, pp. 161-166.
Yeretzian, et al., "Analysing the headspace of coffee by proton-transfer-reaction mass-spectrometry", Int J. Mass Spect, 223-224 (1-3), pp. 115-139, 2003.
Smith, et al., Life Sci., (2004), vol. 74, No. 21, pp. 2593-2604.
Smith, J.C. et al., "Haloperidol: An alternative butyrophenone for nausea and vomiting prophylaxis in anesthesia," AANA Journal 2005, vol. 73, No. 41 pp. 273-275.
Smith, M.T., "Opioid-induced hyperalgesia, opioid rotation and opioid combinations," Acute Pain. vol. 10, pp. 199-200 (2008) [Abstract].
Snyder, et al., "Receptor Mechanisms in Antipsychotic Drug Action: Focus on Sigma Receptors," Journal of Neuropsychiatry, Winter 1989, vol., No. 1, pp. 7-15.
Sonal, G., et al., Ther. Adv. Urol., (2011), vol. 3, No. 1, pp. 19-33.
Souillac, et al., Characterization of Delivery Systems, Differential Scanning Calorimetry, pp. 217-218 (in Encyclopedia of Controlled Drug Delivery, 1999, John Wiley & Sons, pp. 212-227.
Stahl, P.H., et al., "Monographs on Acids and Bases", Handbook of Pharmaceutical Salts: Properties, Selection, and Use, 2002, pp. 265-266, 282-283.
STN—search report—U.S. Appl. No. 11/574,361.
Strupp, et al., "Transdermal fentanyl during high-dose chemotherapy and autologous stem cell support" (2000) Oncology Reports, 7:659-661.
Stubblefield, et al., "Upper-Extremity Pain Disorders in Breast Cancer" (2006) Arch Phys Med Rehabil, vol. 87, Suppl 1, pp. S96-S99.
Su, et al., Pharmacology & Therapeutics, vol. 124, pp. 195-206, 2009.
Sussman, N., "SNRis versus SSRis: Mechanisms of action in treating depression and painful physical symptoms", Primary Care Companion J. Clin. Psychiatry, 2003, 5 (suppl 7), pp. 19-26.
Zahn, P.K., et al., "Mechanisms for Pain Caused by Incisions", Regional Anesthesia and Pain Medicine, 2002, vol. 271 No. 5, pp. 514-516.
Tanda, S., et al., "Pains Resistant to Opioids, and Countermeasures thereof~Including Peripheral Neuropathy Measures of Oxaliplatin", Pharmacy, Oct. 2007, vol. 58, No. 11, pp. 2947-2953 [inc. machine English language translation].

(56) References Cited

OTHER PUBLICATIONS

Taylor, C.P., "Mechanisms of analgesia by gabapentin and pregabalin- calcium channel alpha2-delta [Ca v alpha2-delta]ligands", Pain, 142, 2009, pp. 13-16.
Theoharides, T.C., "Mast cell involvement in interstitial cystitis: a review of human experimental evidence," Urology, (2001), vol. 57, No. 6, pp. 47-55.
Tietze, L., et al., Synthesis, (11), 1079-1080, 1993.
Tramer, M. R., et al., "Efficacy and Adverse Effects of Prophylactic Anti emetics during Patient-Controlled Analgesia Therapy: A Quantitative Systematic Review," Anesth. Analg., 1999, vol. 88, pp. 1354-1361.
Trescot et al., "Opioids in the Management of Chronic Non-Cancer Pain: An Update of American Society of the Interventional Pain Physicians' (ASIPP) Guidelines," Pain Physician. Opioids Special Issue: 11 pp. S5-S62 (2008).
Tyers et al. Oncology 49(4), 263-268 (1992) (Abstract).
Uchitel, O.D., et al., "Acute modulation of calcium currents and synaptic transmission by Gabapentinoids," Channels, 4:6, Nov./Dec. 2010, pp. 490-496.
Van De Merwe, J.P., et al., "Diagnostic criteria, classification, and nomenclature for painful bladder syndrome/interstitial cystitis: an ESSIG proposal", European Urology, 53, 2008, pp. 60-67.
Van Sickle et al. Gastroenterology 121 (4), 767-774 (2001) (Abstract).
Vedejs, E., "Stereochemistry and Mechanism in the Wittig Reaction," Topics in Stereochemistry, 1994, vol. 21, pp. 1-157.
Velucci, "Heterogeneity of Chronic Pain", Clin. Drug Invest. 2012, 32 Suppl. 1, pp. 3-10.
Ventuerello, C., "2-Arylazo-2, 5-dimethyl-3-oxo-2, 3-dihydrof urans, useful intermediates in the synthesis of 1-aryl-5-methyl-3-pyrazolones", Synthesis, 1979, pp. 283-287.
Venturello, C., et al., "A Novel Synthesis of Pyrazol-3-ones Form Biacetyl Dimer and Arenediazonium Salts", Journal of the Chemical Society, Perkin Transactions: Organic and Bio-organic Chemistry, (1972-1999), 7, 681-685, 1978.
Zhang et al. in Synapse 15(4):276-284 (1993), Abstract.
Vinik, A., et al., Nature Clinical Practice Endocrinology & Metabolism, (2006), vol. 2, pp. 2-13.
Vippagunta, et al., Crystalline solids, Advanced Drug Delivery Reviews, 48: 1-26, 2001.
Virmani, et al., Indian Journal of Chemistry, Section B:Organic Chemistry Including Medicinal Chemistry, vol. 17, 1979, pp. 472-477.
Virmani, V. et al., "Methyl-{3-[5-(4-nitro-phenyl)-1-phenyl-1H-pyrazol-3-yl]propyl}-amine", Database Beilstein, Beilstein Institute for Organic Chemistry, Frankfurt-Main, DE, Database accession No. 705147, XP002605613 [X] 1-3,9 * the whole document *.
Virmani, V. et al., "Methyl-{4-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 706821, XP002605614 [X] 1-3,9 * the whole document *.
Virmani, V. et al., "Methyl-{5-[5-(4-nitro-phenyl)-1-phenyl-1H-pyrazol-3-yl]-pentyl}-amine", Database Beilstein, Beilstein Institute for Organic Chemistry, Frankfurt-Main, DE, Database accession No. 710983, XP002605615 [X] 1-3,9 * the whole document *.
Vorobeychik, et al., "Combination Therapy for Neuropathic Pain—A Review of Current Evidence," CNS Drugs, 2011, pp. 1-12.
Wagaw, S., et al. "A Palladium-Catalyzed Strategy For The Preparation of Indoles: A Novel Entry Into The Fischer Indole Synthesis", J. American Chemical Society, 1998, vol. 120, pp. 6621-6622.
Walker, et al., "Sigma Receptors: Biology and Function," Pharmacological Review, 1990, vol. 42, No. 4, pp. 355-402.
Wang, "Opioid-induced hyperalgesia", Chinese Journal of Pain Medicine, 14(3), pp. 129-130 (2008).
Wantuch, C., et al., "Pharmacological validation of a model of cystitis pain in the mouse", Neuroscience Letters, 421, 2007, pp. 250-252.
Wasserheit, C., et al., "Phase II trial of paclitaxel and cisplatin in women with advanced breast cancer: an active regimen with limiting neurotoxicity", Journal of Clinical Oncology, 1996, vol. 14, No. 7 pp. 1993-1999.
Zheng, F.Y., et al. "The Response Of Spinal Microglia To Chemotherapy Evoked Painful Peripheral Neuropathies Is Distinct From That Evoked by Traumatic Nerve Injuries," Neuroscience, 2011, 176, pp. 447-454.
Werling, L.L. et al., "A comparison of the binding profiles of dextromethorphan, memantine, fiuoxotinc and amitriptyline: treatment of involuntary emotional expression disorder," Exp Neurol. Oct. 2007;207 (2):248-57.
Whittington, C.M., et al., Understanding and utilizing mammalian venom via a platypus venom transcriptome. J. Proteomics 2009; 72; 155-164.
European Search Report dated Feb. 1, 2005 in connection with priorirty European Application No. EP 04077421.8.
European Search Report dated Sep. 12, 2008 in connection with European Application No. EP08384006.
European Search Report dated Oct. 2, 2008 in connection with European Application No. EP 08380122.
European Search Report dated Feb. 5, 2010 in connection with European Application No. EP09382144.
European Search Report dated Apr. 14, 2010 in connection with European Application No. EP09382261.
European Search Report dated Apr. 19, 2010 in connection with European Application No. EP10382024.7.
European Search Report dated Jun. 16, 2010 in connection with European Application No. EP 10382023.
European Search Report dated Jul. 1, 2010 in connection with European Patent Application No. EP10382025.
European Search Report dated Oct. 1, 2010 in connection with European Application No. EP10382215.1.
European Search report dated Oct. 22, 2010 by European Patent Office in connection with European Application No. EP 10 38 2148.
European Search Report dated Oct. 29, 2010 in connection with European Application No. EP10382136.
European Search Report dated Jan. 31, 2011 in connection with European Patent Application No. EP10382326.6.
European Search Report dated Mar. 11, 2011 in connection with European Application No. EP10382330.8.
European Search Report dated Oct. 18, 2011 in connection with European Application No. EP11382157.3.
European Search Report dated May 3, 2013 in connection with European Patent Application No. EP13382140.
European Search Report dated Dec. 20, 2013 in connection with European Application No. EP13382246.0.
International Preliminary Report of Patentability with Written Opinion of the International Searching Authority dated Nov. 27, 2012 in connection with International Application No. PCT/EP2011/058633.
International Preliminary Report of Patentability with Written Opinion of the International Searching Authority dated Feb. 14, 2012 in connection with International Application No. PCT/EP2010/061720.
International Preliminary Report of Patentability with Written Opinion of the International Searching Authority dated May 30, 2012 in connection with International Application No. PCT/EP2010/068213.
International Preliminary Report of Patentability with Written Opinion of the International Searching Authority dated Feb. 12, 2013 in connection with International Patent Application No. PCT/EP2011/063583.
International Preliminary Report of Patentability with Written Opinion of the International Searching Authority dated Aug. 7, 2012 in connection with International Application No. PCT/EP11/51643.
International Preliminary Report of Patentability with Written Opinion of the International Searching Authority dated Aug. 24, 2010 in connection with International Application No. PCT/EP2009/001109.

(56) References Cited

OTHER PUBLICATIONS

International Preliminary Report of Patentability with Written Opinion of the International Searching Authority dated Dec. 29, 2015 in connection with International Application No. PCT/EP2014/063360.
International Preliminary Report of Patentability with Written Opinion of the International Searching Authority dated Feb. 28, 2007 in connection with International Application No. PCT/EP2005/009375.
International Preliminary Report of Patentability with Written Opinion of the International Searching Authority dated Jun. 21, 2016 in connection with International Application No. PCT/EP2014/077996.
International Preliminary Report of Patentability with Written Opinion of the International Searching Authority dated Aug. 7, 2012 in connection with International Application No. PCT/EP2011/051644.
International Preliminary Report of Patentability with Written Opinion of the International Searching Authority dated Feb. 3, 2013 in connection with International Application No. PCT/EP2011/063286.
International Preliminary Report of Patentability with Written Opinion of the International Searching Authority dated Jun. 21, 2016 in connection with International Application No. PCT/EP2014/077992.
International Preliminary Report of Patentability with Written Opinion of the International Searching Authority dated Jun. 4, 2013 in connection with International Application No. PCT/EP2011/071584.
International Preliminary Report of Patentability with Written Opinion of the International Searching Authority dated Jun. 26, 2012 in connection with International Application No. PCT/EP2012/059232.
International Preliminary Report of Patentability with Written Opinion of the International Searching Authority dated May 30, 2012 in connection with International Application No. PCT/EP2010/068256.
International Preliminary Report of Patentability with Written Opinion of the International Searching Authority dated Nov. 27, 2012 in connection with International Applications No. PCT/EP2011/058224.
International Preliminary Report of Patentability with Written Opinion of the International Searching Authority dated Oct. 20, 2015 in connection with International Application No. PCT/EP2014/057608.
International Search Report dated Sep. 3, 2015 in connection with International Application No. PCT/EP2014/077992.
International Preliminary Report of Patentability with Written Opinion of the International Searching Authority dated Oct. 26, 2010 in connection with International Application No. PCT/EP2009/054974.
International Preliminary Report of Patentability with Written Opinion of the International Searching Authority dated Oct. 26, 2010 in connection with International Application No. PCT/EP2009/054981.
International Search Report issued by the International Searching Authority dated Apr. 5, 2011 in connection with International Application No. PCT/EP2011/051644.
International Search Report dated Jan. 12, 2005 in connection with International Application No. PCT/EP2005/009375.
International Search Report dated Jun. 17, 2009 in connection with International Application No. PCT/EP2009/054974.
International Search report dated Jul. 7, 2009 in connection with International Application No. PCT/EP2009/001109.
International Search Report dated Jul. 24, 2009 in connection with International Application No. PCT/EP2009/054981.
International Search Report dated Nov. 25, 2010 in connection with International Application No. PCT/EP2010/061720.
International Search Report dated Mar. 8, 2011 in connection with International Applications No. PCT/EP2011/058224.
International Search Report dated Mar. 23, 2011 in connection with International Application No. PCT/EP2010/068213.
International Search Report dated May 4, 2011 in connection with International Application No. PCT/EP2011/051630.
International Search Report dated May 4, 2011 in connection with International Application No. PCT/EP2010/068256.
International Search report dated May 23, 2011 in connection with International Application No. PCT/EP11/51643.
International Search Report dated Aug. 31, 2011 in connection with International Application No. PCT/EP2011/063583.
International Search Report dated Sep. 21, 2011 in connection with International Application No. PCT/EP2011/058633.
International Search Report dated Jan. 16, 2012 in connection with International Application No. PCT/EP2001/071583.
International Search Report dated Jan. 31, 2012 in connection with International Application No. PCT/EP2011/063286.
International Search Report dated Mar. 13, 2012 in connection with International Application No. PCT/EP2011/071584.
International Search report dated Oct. 31, 2014 in connection with International Application No. PCT/EP2014/069370.
International Search Report dated Mar. 6, 2014 in connection with International Application No. PCT/EP2014/057608.
International Search report dated Sep. 17, 2014 in connection with International Application No. PCT/EP2014/063360.
International Search Report dated Feb. 25, 2015 in connection with International Application No. PCT/EP2014/077996.
International Search Report dated May 19, 2011 in connection with International Application No. PCT/EP2012/059232.

\* cited by examiner

USE OF SIGMA LIGANDS IN DIABETES TYPE-2 ASSOCIATED PAIN

This application is a National Stage of PCT/EP12/059232 filed May 18, 2012 and claims the benefit of EP 11382157.3 filed May 19, 2011.

FIELD OF THE INVENTION

The present invention refers to the use of compounds binding to the sigma receptor for the production of a medicament for the prevention and/or treatment of pain and pain-related symptoms associated to diabetes type-2.

BACKGROUND

Diabetes is a metabolic disorder caused by interaction of genetic, environmental, immunological, as well as life-style factors. The World Health Organization estimates that 366 million people worldwide will suffer from diabetes by year 2030 [Wild S. et al., Diabetes Care 2004, 27, 1047-1053].

According to the American Diabetes Association (ADA; http://www.diabetes.org/home.jsp) four major categories of diabetes have been identified including:
- Type 1 diabetes mellitus: The body's fails to produce insulin.
- Type 2 diabetes mellitus: Results from insulin resistance, combined with relative insulin deficiency.
- Gestational diabetes: Occurs during pregnancy.
- Impaired glucose tolerance (i.e. prediabetes): When a person's blood glucose levels are higher than normal but not high enough for a diagnosis of type 2 diabetes.

Diabetic neuropathy comprises a number of conditions affecting peripheral nerves. It is the most common of the long-term diabetic complications. In fact, diabetic neuropathy is now the most common neuropathy in industrialized countries and may be the most common in the world. The prevalence of sensory neuropathic symptoms, particularly pain, is about 30% among patients with diabetes. Moreover, the prevalence of diabetic neuropathy increases with age, from about 5% in patients between the ages of 20 and 29 to approximately 44% in those between the ages of 70 and 79, and with duration of disease, particularly after 20 years. Prevalence is also higher in patients with poor glycemic control. The most prominent manifestations of diabetic neuropathy are pain and trophic ulcers (e.g., diabetic foot ulcers), both of which are associated with considerable morbidity and disability [Said G. Advanced Studies in Medicine 2001, 1 (11), 457-459].

Peripheral neuropathy can result in a loss of sensation that can lead to neuropathic ulcers, and this is a leading cause of amputation [Poncelet A. N., Geriatrics. 2003, 58(6), 16-8, 24-5, 30; Vileikyte L. Diabetes Metab. Res. Rev. 2004, 20 Suppl 1, S13-18].

Diabetic peripheral neuropathy (DPN, also called distal symmetric neuropathy or sensorimotor neuropathy or diabetic polyneuropathy) is one of the most common complications of both type 1 and type 2 diabetes. In a population-based study [Abbott C. A. et al., Diabet. Med. 2002, 19: 377-384], 22% of the diabetic cohort had peripheral neuropathy that was graded as either moderate or severe. Long-standing peripheral neuropathic pain associated with peripheral neuropathy occurs in one of six diabetic subjects [Daousi C. et al., Diabet. Med. 2004, 21, 976-982].

Most preclinical studies evaluating treatment options for DPN have been carried out in streptozotocin-induced diabetic rodents, which resemble type-1 diabetes. However there is evidence that the etiology and pathology of diabetic neuropathy in type-1 and type-2 diabetes may be different [Sima A. A., Front. Biosci. 2008, 13, 4809-4816].

Research using type-2 diabetic animal models has also been carried out, but less frequently than type-1 [Sima A. A. et al., Diabetologia 2000, 43, 786-793; Li F. et al., Neurobiol. Dis. 2006, 22, 669-676; Oltman C. L. et al., Am. J. Physiol. Endocrinol. Metabol. 2005, 289, E113-E122].

Zucker diabetic fatty (ZDF) rat was first described by Shaw et al. [Proc. Soc. Exp. Biol. Med. 1983, 173(1), 68-75] and Friedman et al. [Am. J. Physiol. 1991, 261(6 Pt 1), E782-E788]. Male obese ZDF (fa/fa or ZDF7Drt-fa; Charles River) are homozygous for a missense mutation causing a nonfunctional leptin receptor (fa/fa). ZDF rats develop obesity, initial hyperinsulinemia (insulin resistance) and then overt diabetes at 8-10 weeks of age [Cheng D. et al., Diabetes Obes. Metab. 2005, 7, 307-317]. Several papers have described neurological abnormalities, including slowed conduction velocity and alterations in sensory testing [Li F. et al., Neurobiol. Dis. 2006, 22, 669-676; Oltman C. L. et al., Diabetes Obes. Metab. 2008, 10, 64-74 among others].

In the pathological course of type-2 diabetes often further complications may arise such as peripheral vascular disease, diabetic neuropathy, diabetic foot problems, diabetic retinopathy and nephropathy. At least some of these complications may cause light, moderate or severe pain symptoms which represent a big problem for the many patients suffering from this disease.

About one-half of patients suffering from type-2 diabetes evidence peripheral polyneuropathy (DPN). This chronic disease is not benign and patients with type-2 diabetes suffer from numerous microvascular and macrovascular complications which cause morbidity and mortality.

The consequences of sensory neuropathy include altered perception of thermal, tactile and vibratory stimuli, involving pain-related symptoms that range from hyperalgesia and allodynia to hypoalgesia [Vinik A. et al., Nature Clinical Practice Endocrinology & Metabolism, 2006, 2, 2-13].

In summary, DPN represents a diffuse symmetric and length-dependent injury to peripheral nerves that has major implications for quality of life (QOL), morbidity, and cost from a public health perspective [Boulton A. J. et al., Diabetes Care 2005, 28, 956-962; Gordois A. et al., Diabetes Care 2003, 26, 1790-1795]. DPN affects 16% of patients with diabetes; it is frequently unreported (12.5%) and more frequently untreated or inadequately treated (39%) [Daousi C. et al., Diabet. Med. 2004, 21, 976-982]. DPN presents an ongoing management problem for patients, caregivers, and physicians. Therefore, there is a need to find new ways for the treatment of type-2 diabetes-associated pain.

BRIEF DESCRIPTION OF THE INVENTION

The present invention solves the aforementioned need since it relates to the new use of compounds binding to the sigma receptor for the production of a medicament for the treatment and/or prevention of type-2 diabetes-associated pain as well as pain-related symptoms associated to type-2 diabetes, preferably type-2 diabetes-associated neuropathic pain.

Therefore, one aspect of the present invention relates to a sigma ligand for the use in the treatment and/or prevention of pain associated to type-2 diabetes and related symptoms. Preferably, said type-2 diabetes-associated pain derives from diabetic neuropathy, diabetic retinopathy, diabetic amyotrophy, gastroparesis, diabetic diarrhea, charcot joint, neuropathy of the bladder, diabetic nephropathy and/or diabetic foot problems.

In a preferred embodiment, said sigma ligand has the general formula (I):

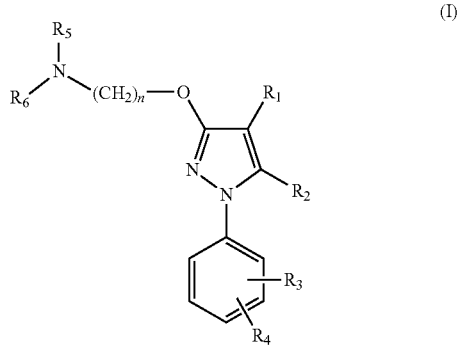

wherein
- $R_1$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
- $R_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;
- $R_3$ and $R_4$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen, or together they form an optionally substituted fused ring system;
- $R_5$ and $R_6$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted, aromatic or non-aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen, or together form, with the nitrogen atom to which they are attached, a substituted or unsubstituted, aromatic or non-aromatic heterocyclyl group;
- n is selected from 1, 2, 3, 4, 5, 6, 7 and 8;
- t is 1, 2 or 3;
- $R_8$ and $R_9$ are each independently selected from hydrogen, substituted or unsubstituted alkyl, substituted or unsubstituted cycloalkyl, substituted or unsubstituted alkenyl, substituted or unsubstituted aryl, substituted or unsubstituted, aromatic or non-aromatic heterocyclyl, substituted or unsubstituted alkoxy, substituted or unsubstituted aryloxy, and halogen;

or a pharmaceutically acceptable salt, isomer, prodrug or solvate thereof.

Another aspect of this invention refers to the use of a sigma ligand, preferably a sigma ligand of formula (I), or a pharmaceutically acceptable salt, isomer, prodrug or solvate thereof, for the manufacture of a medicament for the treatment and/or prevention of type-2 diabetes-associated pain and related symptoms.

Another aspect of the invention is a method for the treatment and/or prophylaxis of type-2 diabetes-associated pain and related symptoms, which comprises administering to the patient in need of such a treatment or prophylaxis a therapeutically effective amount of a sigma ligand, preferably a sigma ligand of formula (I), or a pharmaceutically acceptable salt, isomer, prodrug or solvate thereof.

Another aspect of the invention refers to a medicament or pharmaceutical composition comprising at least one sigma ligand and at least one pharmaceutically acceptable excipient for use in the treatment and/or prevention of type-2 diabetes-associated pain and related symptoms.

Another aspect of the invention refers to a combination of at least one sigma ligand and at least one further active substance for use in the treatment and/or prevention of type-2 diabetes-associated signs and symptoms, including pain.

These aspects and preferred embodiments thereof are additionally also defined in the claims.

DETAILED DESCRIPTION OF THE INVENTION

Figure 1A:
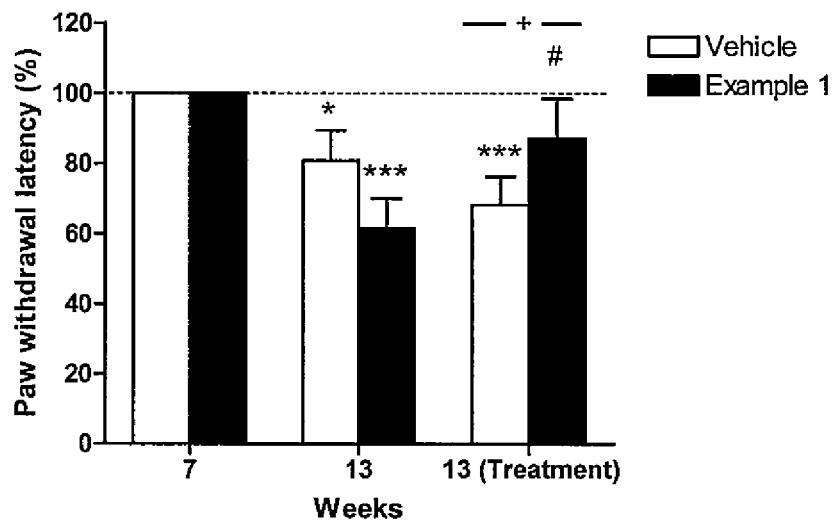
FIG. 1*a*: Effect of the acute treatment with example 1 on thermal hyperalgesia. Bars show the mean %±SEM of modification of the thermal latency (plantar test).

In the context of the present invention, the following terms have the meaning detailed below.

"Alkyl" refers to a straight or branched hydrocarbon chain radical consisting of 1 to 12 carbon atoms, containing no unsaturation, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkyl radicals have from 1 to 6 carbon atoms. If substituted by aryl, it corresponds to an "arylalkyl" radical, such as benzyl or phenethyl. If substituted by heterocyclyl, it corresponds to a "heterocyclylalkyl" radical.

"Alkenyl" refers to a straight or branched hydrocarbon chain radical consisting of 2 to 12 carbon atoms, containing at least one unsaturation, and which is attached to the rest of the molecule by a single bond. Alkenyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. Preferred alkenyl radicals have from 2 to 6 carbon atoms.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple aromatic ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15-membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidized; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine, pyrrole, pyrazole, oxazole, isoxazole, triazole, imidazole, etc.

"Alkoxy" refers to a radical of the formula —$OR_a$ where $R_a$ is an alkyl radical as defined above having one or more (e.g., 1, 2, 3 or 4) oxygen linkages and from 1 to about 12 carbon atoms or preferably 1 to about 6 carbon atoms, e.g., methoxy, ethoxy, propoxy, etc.

"Aryloxy" refers to a radical of formula —O-aryl, where aryl is as previously defined. Some examples of aryloxy compounds are —O-phenyl, —O-p-tolyl, —O-m-tolyl, —O-o-tolyl or —O-naphtyl.

"Amino" refers to a radical of the formula —$NH_2$, —$NHR_a$ or —$NR_aR_b$, optionally quaternized, e.g., methylamino, ethylamino, dimethylamino, diethylamino, propylamino, etc.

"Halogen", "halo" or "hal" refers to bromo, chloro, iodo or fluoro.

References herein to substituted groups in the compounds of the present invention refer to the specified moiety that may be substituted at one or more (e.g., 1, 2, 3 or 4) available positions by one or more suitable groups, e.g., halogen such as fluoro, chloro, bromo and iodo; cyano; hydroxyl; nitro; azido; acyl, such as alkanoyl, e.g. a $C_{1-6}$ alkanoyl group, and the like; carboxamido; alkyl groups including those groups having 1 to about 12 carbon atoms or from 1 to about 6 carbon atoms and more preferably 1-3 carbon atoms; alkenyl and alkynyl groups including groups having one or more (e.g., 1, 2, 3 or 4) unsaturated linkages and from 2 to about 12 carbon or from 2 to about 6 carbon atoms; alkoxy groups having one or more (e.g., 1, 2, 3 or 4) oxygen linkages and from 1 to about 12 carbon atoms or 1 to about 6 carbon atoms; aryloxy such as phenoxy; alkylthio groups including those moieties having one or more (e.g., 1, 2, 3 or 4) thioether linkages and from 1 to about 12 carbon atoms or from 1 to about 6 carbon atoms; alkylsulfinyl groups including those moieties having one or more (e.g., 1, 2, 3 or 4) sulfinyl linkages and from 1 to about 12 carbon atoms or from 1 to about 6 carbon atoms; alkylsulfonyl groups including those moieties having one or more (e.g., 1, 2, 3 or 4) sulfonyl linkages and from 1 to about 12 carbon atoms or from 1 to about 6 carbon atoms; aminoalkyl groups such as groups having one or more (e.g., 1, 2, 3 or 4) N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The compounds of the present invention are preferably in neutral form, the form of a base or acid, in the form of a salt, preferably a physiologically acceptable salt, in the form of a solvate or of a polymorph and/or in the form of in the form of its racemate, pure stereoisomers, especially enantiomers or diastereomers or in the form of mixtures of stereoisomers, especially enantiomers or diastereomers, and/or in any mixing ratio.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to "pharmacologically acceptable salts" or "pharmaceutically acceptable salts".

The term "physiologically acceptable salt" or "pharmaceutically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with $NH_4$.

The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Any compound that is a prodrug of a sigma ligand, in particular a prodrug of a compound of formula (I) is also within the scope of the invention. The term "prodrug" is used in its broadest sense and encompasses those derivatives that are converted in vivo to the compounds of the invention. Examples of prodrugs include, but are not limited to derivatives of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The sigma ligands, in particular the compounds of formula (I) or their salts or solvates, are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As noted previously, the term "pharmaceutically acceptable salts, solvates, prodrugs" refers to any salt, solvate, or any other compound which, upon administration to the recipient is capable of providing (directly or indirectly) a compound as described herein. However, it will be appreciated that non-pharmaceutically acceptable salts, solvates and prodrugs also fall within the scope of the invention since those may be useful in the preparation of pharmaceutically acceptable salts, solvates and prodrugs. The preparation of salts, solvates and prodrugs can be carried out by methods known in the art.

As used herein, the terms "treat", "treating" and "treatment" include in general the eradication, removal, reversion, alleviation, modification, or control of pain and pain-related symptoms associated to diabetes type-2.

As used herein, the terms "prevention", "preventing", "preventive", "prevent" and prophylaxis refer to the capacity of a given substance to avoid, minimize or difficult the onset or development of a pain and pain-related symptoms associated to diabetes type-2 before its onset.

PAIN is defined by the International Association for the Study of Pain (IASP) as "an unpleasant sensory and emotional experience associated with actual or potential tissue damage, or described in terms of such damage" [IASP, Classification of chronic pain, 2nd Edition, IASP Press (2002), 210]. Even though pain is always subjective its causes or syndromes can be classified.

The term "pain" as used in the present invention refers to type-2 diabetes-associated pain.

"Type-2 diabetes-associated pain", as defined in the present invention, preferably includes any form and type of pain/pain syndromes which are related to diabetes type-2. Preferably, said type-2 diabetes-associated pain derives from diabetic neuropathy, diabetic retinopathy, diabetic amyotrophy, gastroparesis, diabetic diarrhea, charcot joint, neuropathy of the bladder, diabetic nephropathy and/or optionally diabetic foot problems.

The term "derived from", as defined in the present invention, has the same meaning as the terms "caused by" and/or "associated with", thereby referring to the consequences of the pathological process/es of diabetes which result in pain.

In a preferred embodiment of the invention said diabetic neuropathy preferably comprises autonomic neuropathy, sensorimotor neuropathy, distal symmetric sensorimotor neuropathy, focal and multifocal neuropathies and/or sensorimotor polyneuropathy.

According to the IASP "allodynia" is defined as "a pain due to a stimulus which does not normally provoke pain" [IASP, Classification of chronic pain, 2nd Edition, IASP Press (2002), 210]. Even though allodynia is commonly recognized as a symptom of neuropathic pain, this is not always necessarily the case so that allodynia not connected to neuropathic pain can occur, though rendering allodynia in some areas broader than neuropathic pain.

The IASP draws the following difference between "allodynia", "hyperalgesia" and "hyperpathia" [IASP, Classification of chronic pain, 2nd Edition, IASP Press (2002), 212]:

| Allodynia | Lowered threshold | Stimulus and response mode differ |
| Hyperalgesia | Increased response | Stimulus and response rate are the same |
| Hyperpathia | Raised threshold; Increased response | Stimulus and response rate may be the same or different |

In a preferred embodiment of the invention said type-2 diabetes-associated pain is allodynia. According to one more particular embodiment, said allodynia is mechanical allodynia. According to another more particular embodiment, said allodynia is thermal allodynia.

In another preferred embodiment of the invention said type-2 diabetes-associated pain is hyperalgesia. According to one more particular embodiment, said hyperalgesia is mechanical hyperalgesia. According to another more particular embodiment, said hyperalgesia is thermal hyperalgesia.

In another preferred embodiment of the invention said type-2 diabetes-associated pain is hyperpathia.

According to the IASP "neuropathy" is defined as "a primary lesion or dysfunction in the nervous system" [IASP, Classification of chronic pain, 2nd Edition, IASP Press (2002), 211]. Neuropathic pain may have central or peripheral origin.

In a preferred embodiment of the present invention said type-2 diabetes-associated pain is derived from neuropathy. According to one more particular embodiment, said type-2 diabetes-associated pain is derived from peripheral neuropathy. According to another more particular embodiment, said type-2 diabetes-associated pain is derived from central neuropathy.

According to the IASP "neuritis" is defined as "Inflammation of a nerve or nerves" [IASP, Classification of chronic pain, 2nd Edition, IASP Press (2002), 212].

In a preferred embodiment of the invention said type-2 diabetes-associated pain derives from neuritis.

According to the IASP "neuralgia" is defined as "pain in the distribution of a nerve or nerves" [IASP, Classification of chronic pain, 2nd Edition, IASP Press (2002), 212].

In a preferred embodiment of the invention said type-2 diabetes-associated pain is identified as neuralgia.

According to the IASP "causalgia" is defined as "a syndrome of sustained burning pain, allodynia and hyperpathia, often combined with vasomotor and sudomotor dysfunction and later trophic changes" [IASP, Classification of chronic pain, 2nd Edition, IASP Press (2002), 210].

In a preferred aspect of the present invention said type-2 diabetes-associated pain is identified as causalgia.

As used herein, the terms "sigma ligand" or "sigma receptor ligand" refer to any compound binding to the sigma receptor.

Said compounds binding to the sigma receptor as defined herein, may be antagonists, inverse agonists, agonists, partial antagonists and/or partial agonists.

The sigma ligand according to the present invention is preferably a sigma receptor antagonist in the form of a (neutral) antagonist, an inverse agonist or a partial antagonist.

In a highly preferred embodiment of the present invention said compounds bind to the sigma-1 receptor.

In a possible embodiment of the present invention the compound binding to the sigma receptor as defined herein is acting on the sigma receptor as a mixed agonist/antagonist.

In another embodiment of the invention the compound binding to the sigma receptor as defined herein is acting on the sigma receptor as an antagonist.

In another embodiment of the invention the compound binding to the sigma receptor as defined herein is acting on the sigma receptor-1 as an antagonist.

In another embodiment of the invention the compound binding to the sigma receptor as defined herein is acting on the sigma receptor as an inverse agonist.

In another embodiment of the invention the compound binding to the sigma receptor as defined herein is acting on the sigma receptor as a partial antagonist.

In another possible embodiment of the invention the compound binding to the sigma receptor as defined herein is acting on the sigma receptor as an agonist.

An "agonist" is defined as a compound that binds to a receptor and has an intrinsic effect and thus, increases the basal activity of a receptor when it contacts the receptor.

A "partial agonist" is defined as a compound which possesses affinity for a receptor, but unlike a full agonist, will elicit only a small degree of the pharmacological response peculiar to the nature of the receptor involved, even if a high proportion of receptors are occupied by the compound.

An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding.

A "partial antagonist" is defined as a compound that binds to the receptor and generates an antagonist response; however, a partial antagonist does not generate the full antagonist response. Partial antagonists are weak antagonists, thereby blocking partially the action of an agonist or inverse agonist on the receptor.

An "inverse agonist" is defined as a compound that produces an effect opposite to that of the agonist by occupying the same receptor and, thus, decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist.

"The sigma receptor's" as used in this application is/are well known and defined using the following citation: "this binding site represents a typical protein different from opioid, NMDA, dopaminergic, and other known neurotransmitter or hormone receptor families" [G. Ronsisvalle et al. Pure Appl. Chem. 2001, 73, 1499-1509]. Pharmacological data based on ligand binding studies, anatomical distribution and biochemical features distinguish at least two subtypes of sigma ($\sigma$) receptors [R. Quiron et al., Trends Pharmacol. Sci.

1992, 13, 85-86; M. L. Leitner, Eur. J. Pharmacol. 1994, 259, 65-69; S. B. Hellewell and W. D. Bowen; Brain Res., 1990, 527, 244-256; G. Ronsisvalle et al. Pure Appl. Chem. 2001, 73, 1499-1509]. The protein sequence of sigma 1 receptor (σ1) is know in the art [e.g. Prasad, P. D. et al., J. Neurochem. 1998, 70, 443-451]. They show a very high affinity to various analgesics (e.g. pentazocine).

"Compound/s binding to the sigma receptor" or "sigma ligand/s" as used in this application is/are defined as a compound having an $IC_{50}$ value of ≤5000 nM, more preferably ≤1000 nM, more preferably ≤500 nM on the sigma receptor. More preferably, the $IC_{50}$ value is ≤250 nM. More preferably, the $IC_{50}$ value is ≤100 nM. Most preferably, the $IC_{50}$ value is ≤50 nM. The half maximal inhibitory concentration ($IC_{50}$) is a measure of the effectiveness of a compound in inhibiting biological or biochemical function. The $IC_{50}$ is the concentration of competing ligand which displaces 50% of the specific binding of the radioligand. Additionally, the wording "Compound/s binding to the sigma receptor", as used in the present application is defined as having at least >50% displacement using 10 nM radioligand specific for the sigma receptor (e.g. preferably [3H]-(+)pentazocine) whereby the sigma receptor may be any sigma receptor subtype. Preferably, said compounds bind to the sigma-1 receptor subtype.

Compounds binding to the sigma receptor, generally also referred to as sigma ligands, are well known in the art. Many of them are encompassed by the "Compound/s binding to the sigma receptor" definition above. Although there are many known uses for sigma ligands, such as antipsychotic drugs, anxiolytics, antidepressants, stroke treatment, antiepileptic drugs and many other indications, including antimigraine and general pain, there is no mention in the art of these compounds as useful for the treatment of pain associated to diabetes type-2.

Examples of well known methods of producing a prodrug of a given acting compound are known to those skilled in the art (e.g. in Krogsgaard-Larsen et al., Textbook of Drug design and Discovery, Taylor & Francis (April 2002)).

In a preferred embodiment, the sigma ligand in the context of the present invention has the general formula (I) as depicted above.

In a preferred embodiment, $R_1$ in the compounds of formula (I) is selected from H, —$COR_8$, and substituted or unsubstituted alkyl. More preferably, $R_1$ is selected from H, methyl and acetyl. A more preferred embodiment is when $R_1$ is H.

In another preferred embodiment, $R_2$ in the compounds of formula (I) represents H or alkyl, more preferably methyl.

In yet another preferred embodiment of the invention, $R_3$ and $R_4$ in the compounds of formula (I) are situated in the meta and para positions of the phenyl group, and preferably, they are selected independently from halogen and substituted or unsubstituted alkyl.

In an especially preferred embodiment of the invention, in the compounds of formula (I) both $R_3$ and $R_4$ together with the phenyl group form an optionally substituted fused ring system (for example, a substituted or unsubstituted aryl group or a substituted or unsubstituted, aromatic or non-aromatic heterocyclyl group may be fused to phenyl group), more preferably, a naphthyl ring system.

Also in the compounds of formula (I), embodiments where n is selected from 2, 3, 4 are preferred in the context of the present invention, more preferably n is 2.

Finally, in another embodiment it is preferred in the compounds of formula (I) that $R_5$ and $R_6$ are, each independently, $C_{1-6}$ alkyl, or together with the nitrogen atom to which they are attached form a substituted or unsubstituted heterocyclyl group, in particular a group chosen among morpholinyl, piperidinyl, and pyrrolidinyl group. More preferably, $R_5$ and $R_6$ together form a morpholine-4-yl group.

In additional preferred embodiments, the preferences described above for the different substituents are combined. The present invention is also directed to such combinations of preferred substitutions in the formula (I) above.

In preferred variants of the invention, the sigma ligand of formula (I) is selected from:

[1] 4-{2-(1-(3,4-Dichlorophenyl)-5-methyl-1H pyrazol-3-yloxy)ethyl}morpholine
[2] 2-[1-(3,4-Dichlorophenyl)-5-methyl-1H-pyrazol-3-yloxy]-N,N-diethylethanamine
[3] 1-(3,4-Dichlorophenyl)-5-methyl-3-[2-(pyrrolidin-1-yl)ethoxy]-1H-pyrazole
[4] 1-(3,4-Dichlorophenyl)-5-methyl-3-[3-(pyrrolidin-1-yl)propoxy]-1H-pyrazole
[5] 1-{2-[1-(3,4-Dichlorophenyl)-5-methyl-1H-pyrazol-3-yloxy]ethyl}piperidine
[6] 1-{2-[1-(3,4-Dichlorophenyl)-5-methyl-1H-pyrazol-3-yloxy]ethyl}-1H-imidazole
[7] 3-{1-[2-(1-(3,4-Dichlorophenyl)-5-methyl-1H-pyrazol-3-yloxy)ethyl]piperidin-4-yl}-3H-imidazo[4,5-b]pyridine
[8] 1-{2-[1-(3,4-Dichlorophenyl)-5-methyl-1H-pyrazol-3-yloxy]ethyl}-4-methylpiperazine
[9] Ethyl 4-{2-[1-(3,4-dichlorophenyl)-5-methyl-1H-pyrazol-3-yloxy]ethyl}piperazine carboxylate
[10] 1-(4-(2-(1-(3,4-Dichlorophenyl)-5-methyl-1H-pyrazol-3-yloxy)ethyl)piperazin-1-yl)ethanone
[11] 4-{2-[1-(4-Methoxyphenyl)-5-methyl-1H-pyrazol-3-yloxy]ethyl}morpholine
[12] 1-(4-Methoxyphenyl)-5-methyl-3-[2-(pyrrolidin-1-yl)ethoxy]-1H-pyrazole
[13] 1-(4-Methoxyphenyl)-5-methyl-3-[3-(pyrrolidin-1-yl)propoxy]-1H-pyrazole
[14] 1-[2-(1-(4-Methoxyphenyl)-5-methyl-1H-pyrazol-3-yloxy)ethyl]piperidine
[15] 1-{2-[1-(4-Methoxyphenyl)-5-methyl-1H-pyrazol-3-yloxy]ethyl}-1H-imidazole
[16] 4-{2-[1-(3,4-Dichlorophenyl)-5-phenyl-1H-pyrazol-3-yloxy]ethyl}morpholine
[17] 1-(3,4-Dichlorophenyl)-5-phenyl-3-[2-(pyrrolidin-1-yl)ethoxy]-1H-pyrazole
[18] 1-(3,4-Dichlorophenyl)-5-phenyl-3-[3-(pyrrolidin-1-yl)propoxy]-1H-pyrazole
[19] 1-{2-[1-(3,4-Dichlorophenyl)-5-phenyl-1H-pyrazol-3-yloxy]ethyl}piperidine
[20] 1-{2-[1-(3,4-Dichlorophenyl)-5-phenyl-1H-pyrazol-3-yloxy]ethyl}-1H-imidazole
[21] 2-{2-[1-(3,4-Dichlorophenyl)-5-phenyl-1H-pyrazol-3-yloxy]ethyl}-1,2,3,4-tetrahydroisoquinoline
[22] 4-{4-[1-(3,4-Dichlorophenyl)-5-methyl-1H-pyrazol-3-yloxy]butyl}morpholine
[23] 1-(3,4-Dichlorophenyl)-5-methyl-3-[4-(pyrrolidin-1-yl)butoxy]-1H-pyrazole
[24] 1-{4-[1-(3,4-Dichlorophenyl)-5-methyl-1H-pyrazol-3-yloxy]butyl}piperidine
[25] 1-{4-[1-(3,4-Dichlorophenyl)-5-methyl-1H-pyrazol-3-yloxy]butyl}-4-methylpiperazine
[26] 1-{4-[1-(3,4-Dichlorophenyl)-5-methyl-1H-pyrazol-3-yloxy]butyl}-1H-imidazole
[27] 4-[1-(3,4-Dichlorophenyl)-5-methyl-1H-pyrazol-3-yloxy]-N,N-diethylbutan-1-amine
[28] 1-{4-[1-(3,4-Dichlorophenyl)-5-methyl-1H-pyrazol-3-yloxy]butyl}-4-phenylpiperidine

[29] 1-{4-[1-(3,4-Dichlorophenyl)-5-methyl-1H-pyrazol-3-yloxy]butyl}-6,7-dihydro-1H-indol-4(5H)-one
[30] 2-{4-[1-(3,4-Dichlorophenyl)-5-methyl-1H-pyrazol-3-yloxy]butyl}-1,2,3,4-tetrahydroisoquinoline
[31] 4-{2-[1-(3,4-Dichlorophenyl)-5-isopropyl-1H-pyrazol-3-yloxy]ethyl}morpholine
[32] 2-[1-(3,4-Dichlorophenyl)-5-isopropyl-1H-pyrazol-3-yloxy]-N,N-diethylethanamine
[33] 1-(3,4-Dichlorophenyl)-5-isopropyl-3-[2-(pyrrolidin-1-yl)ethoxy]-1H-pyrazole
[34] 1-(3,4-Dichlorophenyl)-5-isopropyl-3-[3-(pyrrolidin-1-yl)propoxy]-1H-pyrazole
[35] 1-{2-[1-(3,4-Dichlorophenyl)-5-isopropyl-1H-pyrazol-3-yloxy]ethyl}piperidine
[36] 2-{2-[1-(3,4-Dichlorophenyl)-5-isopropyl-1H-pyrazol-3-yloxy]ethyl}-1,2,3,4-tetrahydroisoquinoline
[37] 4-{2-[1-(3,4-Dichlorophenyl)-1H-pyrazol-3-yloxy]ethyl}morpholine
[38] 2-[1-(3,4-Dichlorophenyl)-1H-pyrazol-3-yloxy]N,N-diethylethanamine
[39] 1-(3,4-Dichlorophenyl)-3-[2-(pyrrolidin-1-yl)ethoxy]-1H-pyrazole
[40] 1-{2-[1-(3,4-Dichlorophenyl)-1H-pyrazol-3-yloxy]ethyl}piperidine
[41] 1-(3,4-Dichlorophenyl)-3-[3-(pyrrolidin-1-yl)propoxy]-1H-pyrazole
[42] 1-{2-[1-(3,4-Dichlorophenyl)-5-methyl-1H-pyrazol-3-yloxy]ethyl}piperazine
[43] 1-{2-[1-(3,4-Dichlorophenyl)-5-methyl-1H-pyrazol-3-yloxy]ethyl}pyrrolidin-3-amine
[44] 4-{2-[1-(3,4-Dichlorophenyl)-4,5-dimethyl-1H-pyrazol-3-yloxy]ethyl}morpholine
[45] 2-[1-(3,4-Dichlorophenyl)-4,5-dimethyl-1H-pyrazol-3-yloxy]-N,N-diethylethanamine
[46] 1-(3,4-Dichlorophenyl)-4,5-dimethyl-3-[2-(pyrrolidin-1-yl)ethoxy]-1H-pyrazole
[47] 1-(3,4-Dichlorophenyl)-4,5-dimethyl-3-[3-(pyrrolidin-1-yl)propoxy]-1H-pyrazole
[48] 1-{2-[1-(3,4-Dichlorophenyl)-4,5-dimethyl-1H-pyrazol-3-yloxy]ethyl}piperidine
[49] 4-{4-[1-(3,4-Dichlorophenyl)-1H-pyrazol-3-yloxy]butyl}morpholine
[50] (2S,6R)-4-{4-[1-(3,4-dichlorophenyl)-1H-pyrazol-3-yloxy]butyl}-2,6-dimethyl morpholine
[51] 1-{4-[1-(3,4-Dichlorophenyl)-1H-pyrazol-3-yloxy]butyl}piperidine
[52] 1-(3,4-Dichlorophenyl)-3-[4-(pyrrolidin-1-yl)butoxy]-1H-pyrazole
[53] 4-[1-(3,4-dichlorophenyl)-1H-pyrazol-3-yloxy]-N,N-diethylbutan-1-amine
[54] N-benzyl-4-[1-(3,4-dichlorophenyl)-1H-pyrazol-3-yloxy]-N-methylbutan-1-amine
[55] 4-[1-(3,4-Dichlorophenyl)-1H-pyrazol-3-yloxy]-N-(2-methoxyethyl)-N-methylbutan-1-amine
[56] 4-{4-[1-(3,4-Dichlorophenyl)-1H-pyrazol-3-yloxy]butyl}thiomorpholine
[57] 1-[1-(3,4-Dichlorophenyl)-5-methyl-3-(2-morpholinoethoxy)-1H-pyrazol-4-yl]ethanone
[58] 1-{1-(3,4-Dichlorophenyl)-5-methyl-3-[2-(pyrrolidin-1-yl)ethoxy]-1H-pyrazol-4-yl}ethanone
[59] 1-{1-(3,4-Dichlorophenyl)-5-methyl-3-[2-(piperidin-1-yl)ethoxy]-1H-pyrazol-4-yl}ethanone
[60] 1-{1-(3,4-Dichlorophenyl)-3-[2-(diethylamino)ethoxy]-5-methyl-1H-pyrazol-4-yl}ethanone
[61] 4-{2-[5-Methyl-1-(naphthalen-2-yl)-1H-pyrazol-3-yloxy]ethyl}morpholine
[62] N,N-Diethyl-2-[5-methyl-1-(naphthalen-2-yl)-1H-pyrazol-3-yloxy]ethanamine
[63] 1-{2-[5-Methyl-1-(naphthalen-2-yl)-1H-pyrazol-3-yloxy]ethyl}piperidine
[64] 5-Methyl-1-(naphthalen-2-yl)-3-[2-(pyrrolidin-1-yl)ethoxy]-1H-pyrazole or their pharmaceutically acceptable salts, isomers, prodrugs or solvates.

In a preferred embodiment of the invention, the sigma ligand of formula (I) is 4-{2-[5-methyl-1-(naphthalen-2-yl)-1H-pyrazol-3-yloxy]ethyl}morpholine. This particular compound is designated in the examples of the present invention as compound no 61.

In a more preferred embodiment, the sigma ligand of formula (I) is the 4-{2-[5-methyl-1-(naphthalen-2-yl)-1H-pyrazol-3-yloxy]ethyl}morpholine hydrochloride. This particular compound is designated in the examples of the present invention as example no 1.

The compounds of formula (I) and their salts or solvates can be prepared as disclosed in the previous application WO2006/021462.

As stated previously, one aspect of this invention refers to the use of a sigma ligand as defined above for the manufacture of a medicament for the treatment and/or prevention of pain associated to type-2 diabetes.

A further aspect of the present invention relates to a medicament or composition in different pharmaceutical forms comprising at least a compound binding to the sigma receptor (preferably a compound of formula (I)), optionally at least one further active substance and at least one pharmaceutically acceptable excipient for use in the treatment and/or prevention of pain associated to type-2 diabetes.

Preferably, the medicament is suitable for oral or parenteral administration, more preferably for oral, intravenous, intraperitoneal, intramuscular, subcutaneous, intrathekal, rectal, transdermal, transmucosal or nasal administration.

Medicaments for oral administration are preferably selected from the group consisting of tablets, drageés, capsules, powders, drops, gels, juices, sirups, solutions and suspensions.

The medicament of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

The respective medicament may—depending on its route of administration—also contain one or more excipients known to those skilled in the art. The medicament according to the present invention may be produced according to standard procedures known to those skilled in the art.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The invention also provides a combination of at least one sigma ligand as defined above and at least one further active substance for use in the treatment and/or prevention of type-2 diabetes-associated signs and symptoms, including pain.

The term "further active substance" refers to any active substance or active pharmaceutical ingredient (API) other than a sigma ligand. According to a preferred embodiment, the "further active substance" is selected from:

Opioids: more preferably oxycodone, tramadol, tapentadol, morphine, hydrocodone, codeine, buprenorfine, fentanyl, remifentanyl or sufentanyl; even more preferably oxycodone, tramadol, tapentadol, morphine or hydrocodone;
Anti-epileptics: more preferably pregabalin, gabapentin or retigabine;
Antidepressants: more preferably duloxetine, amitriptyline or venlafaxine;
Conventional analgesics: more preferably ibuprofen, diclofenac, naproxen, aspirin, desketoprofen or ketoprofen;
Selective COX-2 inhibitors: more preferably celecoxib;
$\alpha_2$-adrenergics: more preferably clonidine; and/or
NMDA inhibitors: more preferably ketamine or memantine.

Another aspect of the invention is a method of treatment of a patient, notably a human, suffering type-2 diabetes-associated pain, or likely to suffer pain as a result of type-2 diabetes, which comprises administering to the patient in need of such a treatment or prophylaxis a therapeutically effective amount of a sigma ligand as defined above.

The following examples are merely illustrative of certain embodiments of the invention and cannot be considered as restricting it in any way.

EXAMPLES

1. Materials and Methods 1.1. Drugs

The example 1 was dissolved in physiological saline (0.9%) and pH was corrected to 5 with NaOH. The compound was administered by the intraperitoneal (i.p.) route. The doses of drug employed in the present study were 64 mg/kg i.p. for acute administration and 25 mg/kg i.p. twice a day (BID) for the chronic treatment during 14 days. The compound and the saline (vehicle) adjusted at pH 5, were administered in a volume of 0.5 ml.

1.2. Animals

All experimental protocols were performed in strict accordance with the EC regulation for care and use of experimental animals (86/609/EEC). Studies were performed with male ZDF (Zucker Diabetic Fatty) rats (ZDF/Gmi, fa/fa) obtained from Charles Rivers Genetic Models Inc. 6 week old rats were housed in groups of two in standard transparent cages, under a 12 light-dark cycle, and animals were maintained on Purina 5008 (16.7 kcal % fat) diet and sterile tap water, available ad libitum. Nonfasting blood glucose levels and body weight were regularly monitored.

2. Treatments 2.1. Acute Treatments

Acute example 1: animals received one injection (0.5 ml) of example 1 (64 mg/kg i.p.) 30 minutes before behavioral testing (n=8).

Control: animals received one vehicle injection (0.5 ml) (0.001% acetic acid solution diluted in physiological saline) 30 minutes before behavioral testing (n=8).

2.2. Chronic Treatments

Chronic example 1: animals received one injection (0.5 ml) of example 1 (25 mg/kg BID, for 14 days) (n=8). Behavioral tests were performed once a week during the treatment, and one week after the last administration they were sacrificed and electrophysiological and cardiovascular experiments were carried out.

Chronic vehicle: animals receiving a vehicle injection (0.5 ml i.p. BID for 14 days) (n=8). Behavioral tests were performed once a week during the treatment, and after the last in vivo determination animal were sacrificed and electrophysiological and cardiovascular experiments were carried on.

3. Procedures 3.1. Behavioral Tests

Plantar Test:

Thermal (heat) hyperalgesia (heat-nociception) was tested using a 37370 plantar test apparatus (Ugo Basile, Comerio VA, Italy). The withdrawal latency from a focused beam of radiant heat applied to the mid plantar surface of the hindpaws was recorded. The intensity of light was adjusted at the start of the experiment such that the control average baseline latencies were about 8 s and a cut-off latency of 30 s was imposed. The withdrawal latency of each paw was measured and the mean value was used for data analysis. The antihyperalgesic effect of the treatment was evidenced as an increase in the withdrawal latency respect to control baseline latencies.

Von Frey Test:

Mechanical allodynia was assessed using an electronic Von Frey apparatus (EVF3, Bioseb, BP89, Chaville Cedez, France). Rats were placed individually on an elevated iron mesh floor, covered by a transparent plastic cage and were allowed to adapt to the testing environment for at least 15 minutes. The test was done by applying the von Frey filament through the mesh floor to the plantar surface of each hindpaw.

The test was performed three times with approximately 3 min interval between trials. The mean of the three trials was used for data analysis. Mechanical allodynia was defined as a significant decrease in the pressure threshold evoking withdrawal of the hindpaw mechanically stimulated. The upper cut-off limit was 50 g.

Spontaneous Locomotor Activity:

it was evaluated using individual photocell activity chambers (Cibertec, Spain). Rats were placed in the recording chambers (55×40 cm, spacing between beams 3 cm) 50 min after drug administration, and the number of interruptions of photocell beams was recorded over a 30-min period.

3.2 Skin—Nerve Preparation and Electrophysiological Recordings

In order to minimize pain or discomfort, animals were killed by cervical dislocation. The saphenous nerve and its innervating territory on the hairy hindpaw skin were subcutaneously dissected and excised. The skin was pinned, corium-side up, in an organ bath, and superfused (16 ml/min) with synthetic interstitial fluid (SIF) [(in mM): 108, NaCl; 3.5, KCl; 0.7, $MgSO_4$; 26, $NaHCO_3$; 1.7, $NaH_2PO_4$; 1.5, $CaCl_2$; 9.6, sodium gluconate; 5.5, glucose; 7.6, sucrose)], which was saturated with carbogen (95% $O_2$-5% $CO_2$), maintained at a temperature of 32±0.5° C. and a pH of 7.38. The saphenous nerve was drawn through a hole into a recording chamber, placed on a small mirror and covered with a layer of paraffin oil. Neuronal activity was recorded using gold-wire electrodes. Small filaments of the nerve were repeatedly split with sharpened forceps until a single unit activity could be recorded from them. The evoked action potentials were amplified, filtered, and led to an oscilloscope and audiomonitor and sent to a PC, through an analog-digital converter, where they were sampled online via a data acquisition system (Microstar DAP 3000a board and SPIKE/SPIDI software package (C. Forster, University of Erlangen—Nurnberg, Germany)). Spikes were later analyzed offline using the SPIDI software.

Units were first identified by manual probing of the skin with a blunt glass rod that exerts a pressure of more than 500 mN to search for their receptive field (RF). Only units responding to this stimulus were then studied in detail. In order to characterize the units, we assessed their conduction velocity (CV) by electrically stimulating the RF with supramaximal square-wave pulses (pulse width, 0.5 ms; train frequency, 0.2 Hz; variable intensity) with a Teflon-coated steel microneurography electrode (shaft diameter 1 mm, bare tip diameter 5-10 μm impedance 1-5 MΩ); an indifferent electrode was placed nearby in the organ bath. The CV of a unit was estimated using the distance and conduction delay between the recording and stimulating electrodes placed on the receptive field.

Once a single unit was identified, it was left to a control period of 1 min in order to record spontaneous activity, defined as a discharge rate ≥1 spike/min and then, mechanical stimulation was applied with a stimulator with plastic cylindrical probe (flat tip; diameter: 1 mm, Cibertec®) that was perpendicularly placed with a micromanipulator on the most sensitive spot of the skinny RF of the unit. Each stimulus began with an adaptation period of 3 s in which the probe of the stimulator was touching the skin but not delivered any pressure.

After the offset of any stimuli, the probe was lifted off the tissue and in order to avoid fibers' damage (desensitization) time interval between two consecutive stimuli along the protocol was 5 min. The stimulation protocol was as follows:

First, the electromechanical threshold of the units, defined as the pressure that evoked the first spike that was followed by another spike within the next 8 mN increment (modified from: Suzuki et al., Neurosci. Res. 2002, 43, 171-178), was determined by application of a ramp-pressure stimulation (constantly increasing stimulus from 0 to 200 mN [Schlegel T. et al., Neurosci. Lett. 2004, 361, 163-167] with a speed of 8 mN/s). For units that showed spontaneous discharges during the 30 s preceding the ramp force stimulus onset, the mean discharge rate in those 30 s was calculated (basal activity, impulses/s (imp/s)) and the threshold was determined as the lowest force at which the instantaneous frequency of spikes continuously exceeded the mean basal activity+SD.

Second, 8 stimuli of constant suprathreshold pressure (~threshold+40 mN, step-pressure stimulation) were delivered for 5 s.

Finally, to explore the thermal sensitivity of the units, when the mechanical stimulation protocol was finished, the response to cold (~11° C.) and noxious heat (~52° C.) were checked by bolus application of a 1 ml of SIF solution at icecold and heat temperatures to the receptive field which was isolated by a selfsealing metal ring (1 cm diameter) and the bath solution inside the ring was removed with a syringe. The temperature reached within the ring was measured with a thermocouple gently placed inside and almost touching the skin. A true cold or heat discharges were scored when the unit discharged at least three action potentials during the application and control applications of fluid at 32° C. did not evoke a discharge. The responses to cold and heat stimuli are only qualitatively reported. The interval between the cold and heat applications was of 5 min.

This study is focused only on those mechanically sensitive afferents units who's CVs were in the myelinated Aδ-fiber range. In agreement with other studies in the rat, units conducting from 2.5 to 24.0 m/s were considered as Aδ. None of the fibers presented a CV>13.5 m/s, that has been considered the limit to distinguish between Aδ- and Aβ-fibers.

To analyze the mechanical response to the step-pressure stimulation and in order to avoid pressure fluctuations, the spikes elicited by the first and last seconds of each stimulus were not included in the total spike counting.

4. Data and Statistical Analysis

Plantar test results are expressed as the percentage of the mean of thermal latency obtained from both hindpaws.

Von Frey test results are expressed as the percentage of the mean of mechanical threshold obtained from both hindpaws.

Spontaneous locomotor activity is expressed as the percentage of the mean number of crossings of the photocell beams over 30 minutes.

Data are expresses as mean+standard error mean (SEM). Statistical analysis of drug effects for significant differences between multiple groups were performed by analysis of variance (ANOVA), followed, when appropriate, by post-hoc Newman-Keuls test or Bonferroni Test. $P<0.05$ was considered as statistically significant.

Example 1

Synthesis of 4-{2-[5-methyl-1-(naphthalen-2-yl)-1H-pyrazol-3-yloxy]ethyl}morpholine (Compound 61) and its Hydrochloride Salt

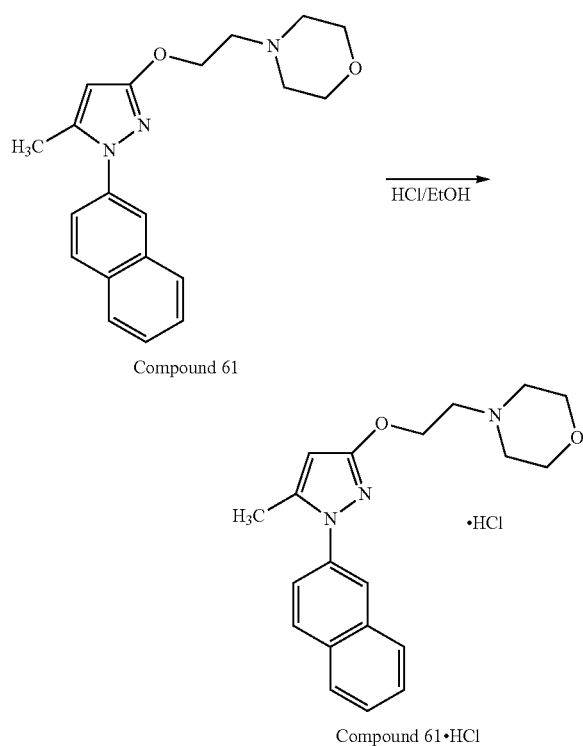

Compound 61

Compound 61·HCl

Compound 61 can be can be prepared as disclosed in the previous application WO2006/021462. Its hydrochloride can be obtained according the following procedure:

Compound 61 (6.39 g) was dissolved in ethanol saturated with HCl, the mixture was stirred then for some minutes and evaporated to dryness. The residue was crystallized from isopropanol. The mother liquors from the first crystallization afforded a second crystallization by concentrating. Both crystallizations taken together yielded 5.24 g (63%) of the corresponding hydrochloride salt (m.p.=197-199° C.).

$^1$H-NMR (DMSO-$d_6$) δ ppm: 10.85 (bs, 1H), 7.95 (m, 4H), 7.7 (dd, J=2.2, 8.8 Hz, 1H), 7.55 (m, 2H), 5.9 (s, 1H), 4.55 (m, 2H), 3.95 (m, 2H), 3.75 (m, 2H), 3.55-3.4 (m, 4H), 3.2 (m, 2H), 2.35 (s, 3H).

HPLC purity: 99.8%

Example 2

Effect of the Acute Treatment with Example 1 on Nociception and Motility (FIG. 1)

Figure 1B:
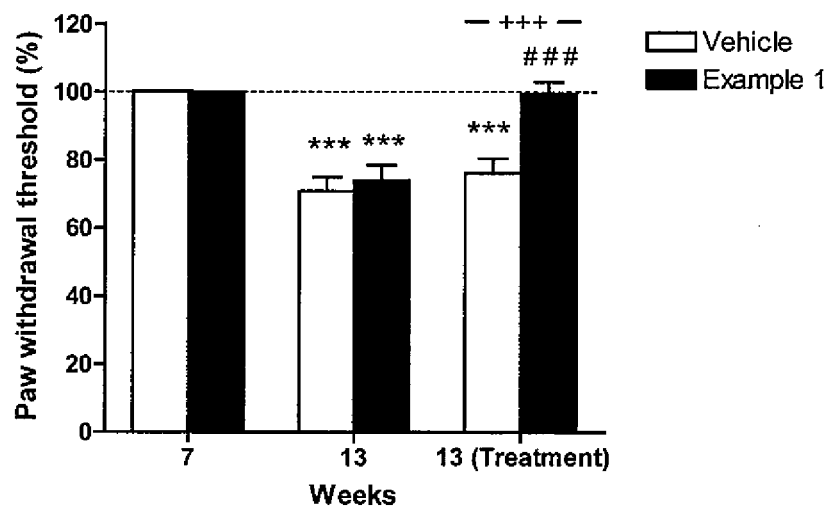
FIG. 1 *b*: Effect of the acute treatment with example 1 on mechanical allodynia. Bars show the mean %±SEM of modification of the threshold of response to mechanical stimulation (Von Frey test).
FIG. 1*c*: Effect of the acute treatment with example 1 on spontaneous locomotor activity. Bars show the mean %±SEM of modification of the total number of crosses (spontaneous motility).
Figure 1C:
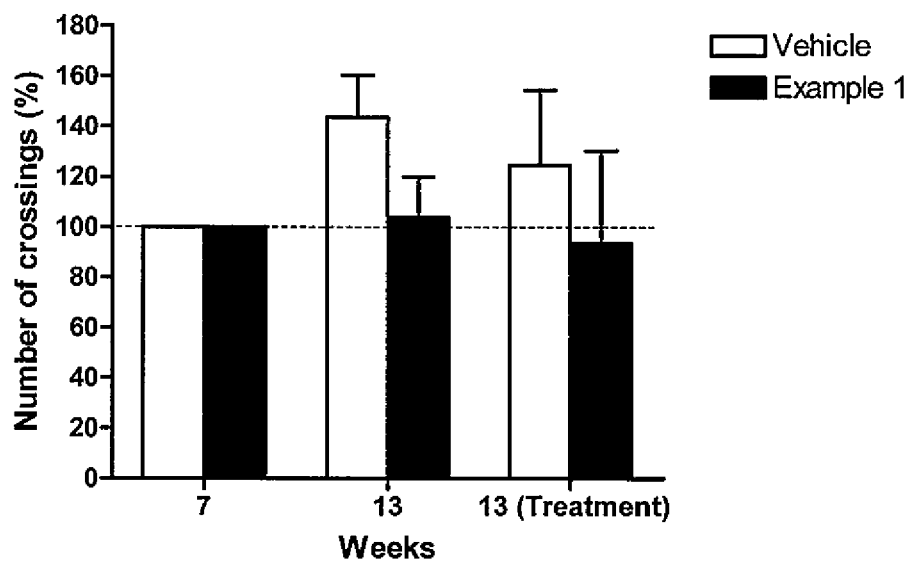

Nociception and motility of ZDF rats aged 7 weeks (before neuropathy), 13 weeks (after neuropathy was developed) and the effect induced by one i.p. administration of example 1 (64 mg/kg) or vehicle are shown in FIGS. 1a-1c. Control values are normalized (control groups=100) in order to simplify the comparison. Statistical differences have been calculated using Bonferroni's Multiple Comparison Test post-two way ANOVA and are labeled as follows: * vs. corresponding group of week 7; # vs. corresponding group of week 13; + vs. vehicle (week 13).

ZDF rats showed mean blood glucose concentration (mg/dL) on week 7 of 91.8±8.6 for the group of rats assigned to receive treatment with example 1 and of 84.4±7 for those assigned to be treated with the vehicle. Six weeks later (week 13) glucose levels were already significantly higher in both groups 414.3±46.2% and 412.9±18.9%, respectively.

The ZDF rats developed significant thermal hyperalgesia (FIG. 1a) and mechanical allodynia (FIG. 1b) by the 13th week and acute i.p. treatment with example 1 at 64 mg/kg restored baseline values found at the 7th week (before the development of type-2 diabetes and thus type-2 diabetic neuropathy and pain).

Example 1 at dose of 64 mg/kg i.p. administered 30 minutes before tests in ZDF rats significantly increased the latency to hindpaw withdrawal (i.e., reversed thermal hyperalgesia) in response to thermal stimulation: 25.5±9.1% for Example 1-treated compared to 12.6±6.9% for vehicle-treated animals (FIG. 1a).

With respect to mechanical allodynia, the pressure threshold evoking withdrawal response was reduced in ZDF rats aged 13 weeks (29.2±3.1% reduction in the group assigned to be treated with vehicle and 26.1±4.5 reduction in the group assigned to be treated with Example 1) when compared with values recorded in rats aged 7 weeks. The threshold was significantly increased (i.e., the mechanical allodynia was reversed) by treatment with compound example 1, returning to basal values found by week 7 (FIG. 1 b).

The spontaneous locomotor activity was not significantly different in none of the analyzed groups (FIG. 1c).

Example 3

Effect of the Chronic Treatment with Example 1 on Nociception and Motility (FIG. 2)

Figure 2A:
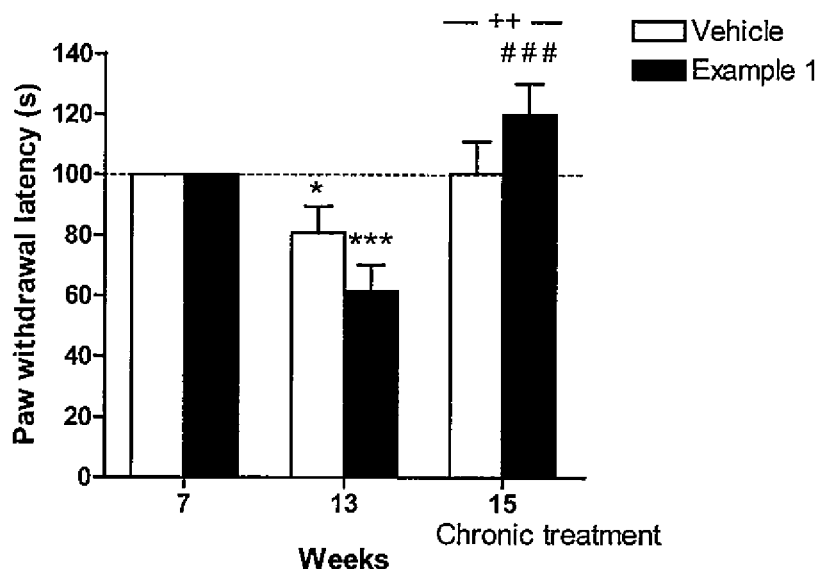
FIG. 2*a*: Effect of the chronic treatment with example 1 on thermal hyperalgesia. Bars show the mean %±SEM of modification of the thermal latency (plantar test).
Figure 2B:
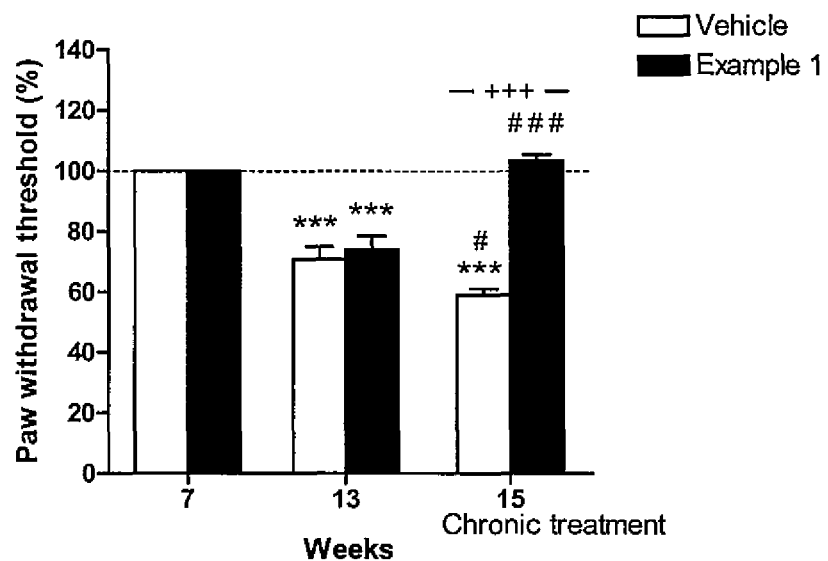
FIG. 2*b*: Effect of the chronic treatment with example 1 on mechanical allodynia. Bars show the mean %±SEM of modification of the threshold of response to mechanical stimulation (Von Frey test).
Figure 2C:
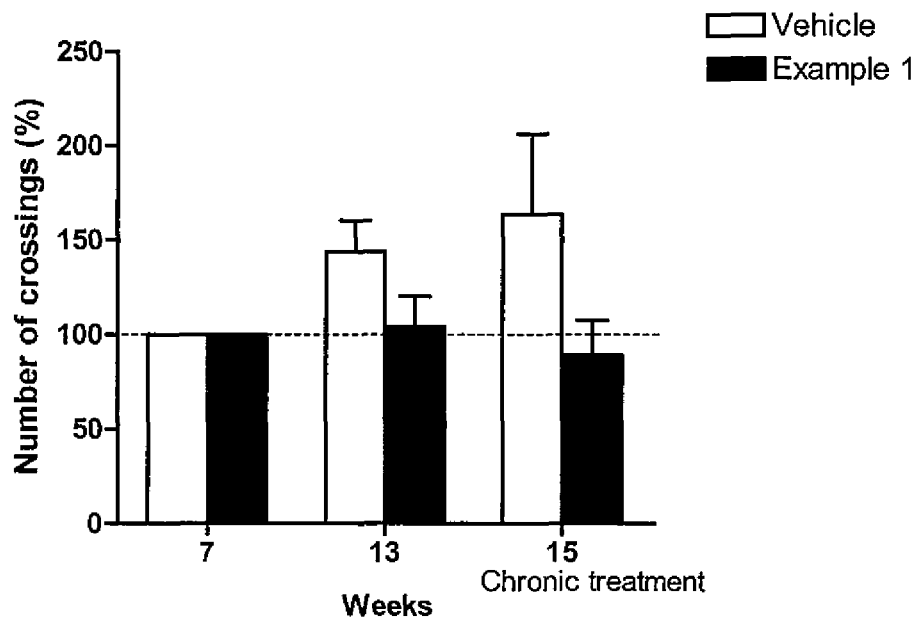
FIG. 2*c*: Effect of the chronic treatment with example 1 on spontaneous locomotor activity Bars show the mean %±SEM of modification of the total number of crosses (spontaneous motility).

Nociception and motility of ZDF rats aged 7 weeks (before neuropathy), 13 weeks (after neuropathy was developed) and the effect induced by i.p. administration of example 1 (25 mg/kg) or vehicle twice a day during 14 days (week 13 to 15) are shown in FIGS. 2a-2c. Control values are normalized (control groups=100) in order to simplify the comparison. Statistical differences have been calculated using Bonferroni's Multiple Comparison Test post-two way ANOVA and are labeled as follows: * vs. corresponding group of week 7; # vs. corresponding group of week 13; + vs. vehicle (week 13).

The compound example 1 (25 mg/kg i.p, BID) was administered for 14 days and the effect of this treatment on nociception and on spontaneous motility was 14 days after the first injection. Treatment began on week 13, when neuropathy was already developed.

After 14 days of example 1 administration, thermal hyperalgesia (FIG. 2a) and mechanical allodynia (FIG. 2b) were completely reversed and the recorded values were similar to those obtained before neuropathy was developed (7 weeks of age).

There were no differences in spontaneous locomotor activity between pretreatment values and those recorded on example 1 or vehicle-treated groups (FIG. 2c).

Example 4

Effect of the Chronic Treatment with Example 1 on Peripheral Electrophysiological Recordings (FIG. 3)

Figure 3A:
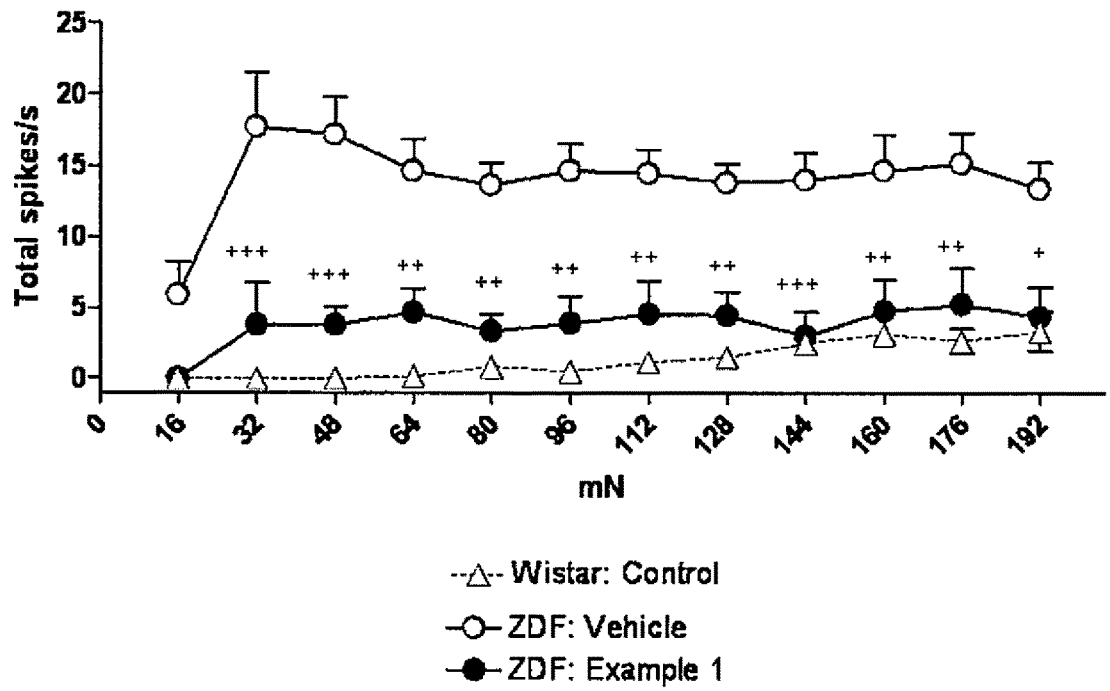
FIG. 3*a*: Effect of the chronic treatment with example 1 on mechanical stimulation of increasing force (Electromechanical threshold; Ramp).
Figure 3B:
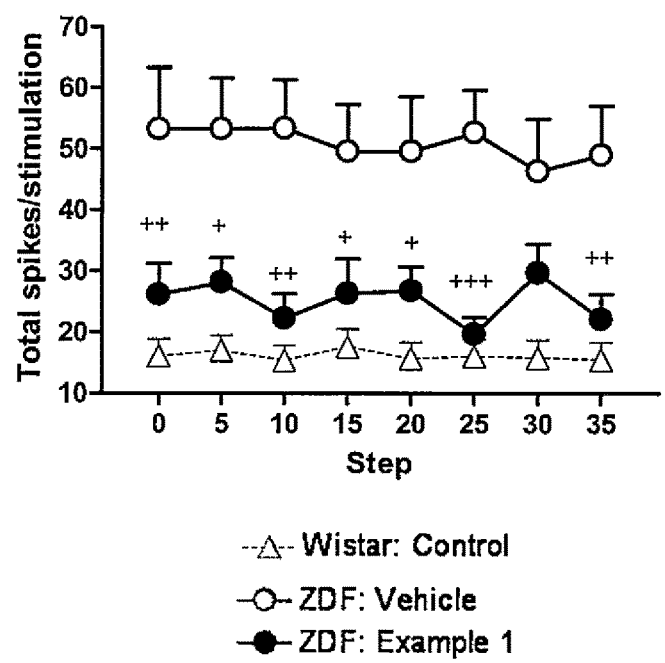
FIG. 3b: Effect of the chronic treatment with example 1 on mechanical stimulation using repeated stimulus (steps) applying innocuous force (Constant suprathreshold pressure; Step)
Figure 3C:
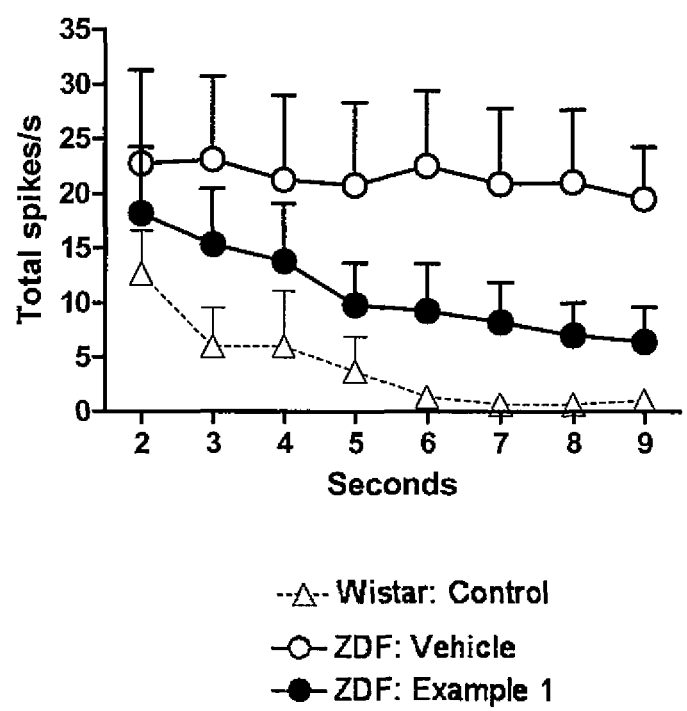
FIG. 3c: Effect of the chronic treatment with example 1 on mechanical stimulation using repeated stimulus (steps) applying nocive force (Constant supramaximal pressure; Nocive Step).

The effect of the chronic treatment with example 1 on the electrophysiological response of nociceptors is shown in FIGS. 3a-3c. Tissues were obtained from Wistar rats (non-diabetic rats) and from ZDF rats after i.p. administration of example 1 (25 mg/kg) or vehicle BID for 14 days. Statistical differences are calculated using Bonferroni's Multiple Comparison Test post-two way ANOVA and are labeled as + for example 1 vs. vehicle.

In the vehicle-treated group of ZDF rats there was a significant increase of the peripheral electrophysiological response to mechanical stimulation as seen in all stimulation protocols (FIGS. 3a-3c) when compared with responses recorded in control Wistar (non-diabetic) rats.

Example 1 administered at 25 mg/kg i.p, BID, for 14 days to ZDF rats reduced the threshold of response to the mechanical stimulation and increased the electrophysiological response (total number of spikes) evoked by mechanical stimulation in comparison with vehicle-treated ZDF rats (FIGS. 3a to 3c).

From the above experimental data it can be concluded that:

a) The ZDF rats developed mechanical allodynia and thermal hyperalgesia, these modifications are considered reliable signs of peripheral neuropathy.
b) The single administration of the example 1 (64 mg/kg, i.p.) reversed the changes in the thresholds for mechanical allodynia and thermal hyperalgesia. Values recorded after example 1 administration were similar to those obtained before the development of neuropathy.
c) No tolerance to the antiallodynic and antihyperalgesic effects exerted by compound Example 1 developed following chronic treatment at a dose of 25 mg/kg for 14 days, twice a day.
d) The inhibitory effects exerted by Example 1 on mechanical allodynia and thermal hyperalgesia were not masked by unspecific effects on locomotor activity.
e) The mechanical allodynia in the behavioral tests correlates with the electrophysiological hyperreactivity recorded on Aδ-fibres in response to mechanical stimulation. Accordingly, the inhibitory effect of compound Example 1 on mechanical allodynia in behavioral tests correlates with a reduction of the hyperreactivity in response to mechanical stimulation found in electrophysiological recordings.

The invention claimed is:

1. A method for treating type-2 diabetes-associated pain selected from the group consisting of allodynia, hyperalgesia and hyperpathia, the method comprising:
   administering a therapeutically effective amount of 4-{2-[5-Methyl-1-(naphthalen-2-yl)-1H-pyrazol-3-yloxy]ethyl}morpholine, a pharmaceutically acceptable salt thereof, or solvate thereof to a patient in need thereof.

2. The method according to claim 1,
   wherein the type-2 diabetes-associated pain is derived from at least one condition selected from the group consisting of diabetic neuropathy, diabetic retinopathy, diabetic amyotrophy, gastroparesis, diabetic diarrhea, charcot joint, neuropathy of a bladder, diabetic nephropathy, and a diabetic foot problem.

3. The method according to claim 1, comprising:
   administering at least one additional active substance to the patient in need thereof.

4. The method according to claim 3,
   wherein the type-2 diabetes-associated pain is derived from at least one condition selected from the group consisting of diabetic neuropathy, diabetic retinopathy, diabetic amyotrophy, gastroparesis, diabetic diarrhea, charcot joint, neuropathy of a bladder, diabetic nephropathy, and a diabetic foot problem.

5. The method according to claim 1, comprising administering a pharmaceutically acceptable salt of 4-{2-[5-Methyl-1-(naphthalen-2-yl)-1H-pyrazol-3-yloxy]ethyl}morpholine.

6. The method according to claim 1, comprising administering 4-{2-[5-Methyl-1-(naphthalen-2-yl)-1H-pyrazol-3-yloxy]ethyl}morpholine hydrochloride.

* * * * *

UNITED STATES PATENT AND TRADEMARK OFFICE
CERTIFICATE OF CORRECTION

Page 1 of 1

PATENT NO. : 9,789,117 B2
APPLICATION NO. : 14/118704
DATED : October 17, 2017
INVENTOR(S) : Jose Miguel Vela Hernandez et al.

It is certified that error appears in the above-identified patent and that said Letters Patent is hereby corrected as shown below:

On the Title Page

Item (30), the Foreign Application Priority Data Information is incorrect. Item (30) should read:
-- (30)  Foreign Application Priority Data
May 19, 2011   (EP) ........................ 11382157 --

Signed and Sealed this
First Day of May, 2018

Andrei Iancu
*Director of the United States Patent and Trademark Office*